United States Patent [19]

Nafarrate et al.

[11] Patent Number: 5,291,013
[45] Date of Patent: Mar. 1, 1994

[54] FIBER OPTICAL MONITOR FOR DETECTING NORMAL BREATHING AND HEARTBEAT MOTION BASED ON CHANGES IN SPECKLE PATTERNS

[75] Inventors: Antonio B. Nafarrate, San Jose; Eric G. Rawson, Saratoga, both of Calif.

[73] Assignee: Alamed Corporation, Portola Valley, Calif.

[21] Appl. No.: 975,853

[22] Filed: Nov. 13, 1992

Related U.S. Application Data

[63] Continuation-in-part of Ser. No. 802,868, Dec. 6, 1991, Pat. No. 5,212,379.

[51] Int. Cl.$^5$ .............................. H01J 40/14
[52] U.S. Cl. .................... 250/227.14; 250/227.16; 128/691
[58] Field of Search ........... 250/227.14, 227.16, 250/227.19, 227.11; 128/691, 666, 714

[56] References Cited

U.S. PATENT DOCUMENTS

| | | | |
|---|---|---|---|
| 3,517,999 | 6/1970 | Weaver | 356/32 |
| 4,169,462 | 10/1979 | Strubé | 128/721 |
| 4,297,684 | 10/1981 | Butter . | |
| 4,339,661 | 7/1982 | Pitt et al. . | |
| 4,843,233 | 6/1989 | Jeunhomme . | |
| 4,986,671 | 1/1991 | Sun et al. | 250/227.14 |
| 5,088,501 | 2/1992 | Niewisch | 128/721 |
| 5,134,281 | 7/1992 | Bryenton et al. | 250/227.14 |

Primary Examiner—David C. Nelms
Assistant Examiner—Que T. Le
Attorney, Agent, or Firm—Oblon, Spivak, McClelland, Maier & Neustadt

[57] ABSTRACT

A fiber optic body motion monitor in which light is transmitted through an optical fiber waveguide physically coupled to a body being monitored, and modal noise at the output of the optical fiber waveguide is applied to a photodetector filtered, rectified and analyzed to detect breathing and heartbeats. Detection of breathing is performed by low-pass filtering the rectified and filtered signal, and adaptive thresholding of the low-pass filtered signal. A similar but separate technique is used to detect heartbeats. In one embodiment, reliability of detection is enhanced by reducing the number of speckles of light applied to the photodetector to approximately 50%, thereby to maximize modal noise current. In another embodiment the photodetector has two halves separately illuminated by approximately two-thirds of the light from the optical fiber waveguide. Outputs of the photodetector halves are applied to the positive and negative inputs of an operational amplifier, whereby common mode noise is eliminated and modal noise current and therefore sensitivity of modal noise detection increased.

61 Claims, 10 Drawing Sheets

FIBER OPTICAL MONITOR FOR DETECTING NORMAL BREATHING AND HEARTBEAT MOTION BASED ON CHANGES IN SPECKLE PATTERNS

CROSS REFERENCE TO RELATED APPLICATIONS

This application is a continuation-in-part of related commonly owned copending U.S. patent application Ser. No. 07/802,868 filed Dec. 6, 1991 U.S. Pat. No. 5,212,379.

BACKGROUND OF THE INVENTION

1. Field of the Invention

The invention relates to a motion monitor based on detection of modal noise produced by minute motions in a single- or multimode-optical fiber illuminated by a coherent or partially coherent light source, and more particularly to such a motion monitor for detecting body motions due to breaths, heartbeats, and determining breathing rate and heart rate.

2. Discussion of Background

A significant cause of death in infants (birth to about 2 years) is "Crib Death" or Sudden Infant Death Syndrome (SIDS). Medical authorities generally agree that some infants simply stop breathing during sleep (apnea) or their heart rates fall dangerously low (bradycardia) and that death from these conditions can be prevented if the condition is detected and help is provided within a short time (one or two minutes) by trained personnel or parents.

Apnea monitors already exist, but their cost creates an affordability problem that limits their use. Also, the existing monitors tend to be unreliable, typically having high false positive rates. Also, existing monitors are obtrusive and difficult to use because the subject must wear a belt or other device connected to the monitor. This further limits their use.

Of interest in the patent literature are U.S. Pat. No. 4,297,684 to Butter, U.S. Pat. No. 4,843,233 to Jeunhomme and U.S. Pat. No. 4,854,706 to Claus et al.

Butter discloses a fiber optic intruder alarm system for protecting the perimeter of an area utilizing a multimode optic fiber as a deformable sensing element, wherein a length of multimode optic fiber is buried in the ground, coherent light is directed through the buried optic fiber and the speckled output light pattern of the fiber is rectified, integrated and threshold detected to determine the presence of an intruder.

Jeunhomme discloses a fiber optic vibration detecting device, but with no means for quantifying the output of the optic fiber, and suggests that observed vibrations can be used to trigger an alarm and/or lighting in the case of a breathing deficiency of a monitored patient.

Claus et al disclose a modal domain optical fiber sensor for vibration monitoring and as a mechanical motion sensor. Claus et al teach filtering the speckle pattern at the output of an optical fiber to a single lobe, termed a single speckle or a single correlation cell elsewhere in the scientific literature, and finds application to monitoring force on mechanical structures, such as a cantilever beam.

However, in the prior art, how to reliably derive information relating to breaths, heartbeats, breathing rate, or heart rate of a monitored person is not well documented, and a need exists for such a monitor which is both inexpensive and reliable.

SUMMARY OF THE INVENTION

Accordingly, one object of this invention is to provide a new and improved body monitor which is reliable, easy to use and inexpensive.

Another object of this invention is to provide a novel body monitor which is capable of measuring and monitoring a subject's breaths, heartbeats, breathing rate, and heart rate.

Yet a further object of this invention is to provide a novel monitor employing improved processing by which abnormalities in either breathing or heartbeat of a patient can be detected and an alarm activated.

These and other objects are achieved according to the present invention by providing a novel monitoring device based on detection of modal noise produced by minute motions in a single mode- or multimode-optical fiber illuminated by a coherent or partially coherent light source such as a laser. The device includes a few meters or tens of meters of fiber which is woven into or attached to a blanket, mattress cover, seat cover or other convenient materials, or clothing pieces in close proximity to the individual being monitored. Coherent light from a gas laser or a laser diode is injected at the input end of the fiber and spatially or polarization filtered at the output end to maximize noise current. This filtered laser light then illuminates a photodiode (i.e., a photo detector). That is, the photodiode detects the optical power in either a near-field or far-field speckle pattern in an area corresponding typically to approximately 27–74% of the speckle "cells," or speckle correlation areas. Filtering is performed either using a spatial filter or, alternatively, a polarizing filter is placed between the detector and the fiber's output end, which passes about half the guided light, namely, that light which is polarized in the direction which is transmitted by the polarizing filter. In this way the photo detector generates a fluctuating signal whose amplitude and frequency spectrum are related to mechanical motions of the fiber.

In practice, normal respiration or cardiac motions will induce small bendings in the fiber, changing the speckle pattern and producing in the photodiode a corresponding "modal noise" signal. This signal may be a voltage signal or a current signal, depending on the type of electronic circuit in which the detector is used. Without loss of generality, and for simplicity henceforth, we will refer simply to this signal as the "noise current." The highest frequency with which the detected noise current fluctuates will be proportional to the velocity of motion of the fiber. Thus, normal breathing will be characterized by a periodic substantial increase in the power of the higher frequency components of the detected noise current. Perturbed respiration, on the other hand, will produce a significantly different noise current spectrum versus time, as will of course cessation of breathing. This persistent abnormality in the frequency spectrum of the noise current can be used to electronically trigger a suitable alarm or alarms, summoning timely aid.

In addition to detecting apnea it will be observed by those skilled in the art that this invention is also capable of detecting, and triggering an appropriate alarm response to, other breathing anomalies such as rapid or otherwise distressed breathing, as well as irregular, too rapid, too slow, or arrhythmic heartbeat. Such other alarm(s) could conveniently be distinct from the apnea alarm. If multiple conditions and/or plural individuals are being monitored simultaneously, easily discernible alarms could be used to facilitate the identification of the reason and source for any alarm that is given.

Additionally, a device of the foregoing type can also be used to monitor certain normal bodily functions. Examples are the monitoring of normal respiration and heartbeat in a medical treadmill test, and around-the-clock monitoring of respiration and/or heartbeat by attaching the invention to an ambulatory recording device or a wireless transmitting device which transmits data from the individual that is being monitored to a remote recording device. The device of the present invention can also be used to monitor heart rate and breathing rate over the course of a period of sleep to assist in the diagnosis of sleep disorders. Also, it could simply be used to detect the presence or absence of a subject simply based on the presence or absence of breathing or a heartbeat, such as in a nursing home or home care setting where patient location is required to be known.

Furthermore, such a device can also be used to monitor the motions of animals other than humans or of non-animate objects, such as machines with moving mechanical parts.

The longer the sensor portion of the optical fiber that is used (that is, that portion comprising the middle section that is mechanically attached to the object or individual being monitored, and excluding the input and output ends), the greater will be the sensitivity of the output speckle pattern to movements of the object or individual being monitored, and the higher will be the frequency components in the noise current which convey useful information. The longer the fiber, however, the greater will be its purchase and assembly costs and its optical attenuation of the laser light which propagates through it. Thus, the optimal length of optical fiber used in this invention will be governed by a balance of these factors. Lengths of the order of a few meters to a few tens of meters have been found to be suitable.

The present invention includes improved processing circuits by which breathing and/or heartbeat abnormalities can be reliably detected. Laser light at the output of the optic fiber is spatially or polarization filtered to maximize modal noise current in the photodiode and generates noise current signals that are applied to a primary bandpass filter having a passband chosen to match the design of the sensor in use. For example, a sensor using 20 meters of plastic step-index with a core diameter of 0.5 mm and a numerical aperture (NA) of 0.5 was found to have a preferred passband of about 23–200 Hz, optimally 33–133 Hz. Another sensor using 20 meters of silica core step index fiber with a core diameter of 0.2 mm and an NA of 0.37 was found to have a preferred passband of about 13–120 Hz, optimally 20–80 Hz. From a generic standpoint, the object of the primary bandpass filter is to pass signals in a passband in which breathing and/or heartbeat signals have significant content. As determined experimentally, this passband varies as a function the structure of the sensor used. Therefore, according to the present invention the passband can be determined based on a frequency, $f_{max}$, at which the change in noise power between breathing and non-breathing states and heartbeat and non-heartbeat states is greatest. The passband should then be set to $0.33\ f_{max} < f_{max} < 3.0\ f_{max}$, and preferably between $0.5$ and $2.0\ f_{max}$. In the experimental examples herein described $f_{max}$ was 67 Hz for the first design described and 40 Hz for the second design described and the passbands should be determined based on the ranges given.

The primary passband filtered signal is then rectified by a full-wave rectifier, sometimes called an absolute value circuit. The rectified signal is then applied to two extraction circuits, including a heartbeat extraction circuit in which the rectified signal is passed to an adjustable secondary bandpass filter having a passband in the range 0.8 Hz–5.0 Hz, preferably ~1–3 Hz. The output of the secondary bandpass filter is applied to a peak detector, and detected peaks are then compared to a threshold to determine the existence of a heartbeat event. The rectified signal is also applied to a breath event extraction circuit connected in parallel to the heartbeat extraction circuit and including an optional secondary low pass filter passing frequencies below ~0.5 Hz, and an adaptive threshold circuit by which the processed signal is compared to an adaptable threshold which varies in relation to the recent maximum and minimum amplitudes of the signal at the output of the secondary filter.

Alternatively, another embodiment makes use of the fact that light of different, orthogonal polarizations is guided by the optical fiber. As is well known, each spatial mode (that is, each independent optical path) of a dielectric optical fiber is in actuality two modes, corresponding to each of the two possible transverse orthogonal polarizations of the light. It is common practice in the literature to ignore this polarization duality of a fiber's spatial modes when polarity is not substantive to the issue at hand, just as we have done to this point. However, we now consider the effects of that polarization duality.

Just as light power can shift from one spatial mode to another, giving rise in the speckle pattern to exchange of intensity between speckle correlation cells, so too can optical power be exchanged between orthogonally polarized modes. In this embodiment of the invention, a polarizing element (for example a piece of common plastic polarizing film) is placed between the fiber output end and the detector. In this way, exactly half the modes are blocked (those with polarizations blocked by the polarizer), and the other half reach the detector. We have discovered analytically, and verified experimentally, that such polarization filtration is equally and equivalently effective in generating modal noise currents in the photocell output as is any form of 50% spatial filtration: for example, 50% spatial filtration by moving a detector back and away from the fiber output end until the detector area subtends 50% of the solid angle of the light emerging from the fiber, or by interposing a mask which blocks 50% of the speckle pattern light from falling on the detector; or by positioning a so-called "Ronchi ruling" between the fiber output and the detector.

As is well known, Ronchi rulings are transparent plates (usually glass or plastic) on which are marked parallel opaque stripes such that the stripe widths equal the adjacent gap widths, so that the transmission is 50%. Such rulings are typically characterized by the number of "line pairs" (one clear stripe plus one opaque stripe constitute a "line pair") per inch (lp/in). We have found Ronchi rulings with 50 lp/in and 150 lp/in to be equally suitable for spatial filtration in this application. It should be noted that our use of Ronchi rulings was for experimental purposes; while it is possible to use Ronchi rulings in practicing this invention, those systems which do so are not preferred embodiments because simpler embodiments exist which perform as well, as will be clarified below.

In yet another embodiment of this invention a "split detector", that is, a detector having two independent and equal sized photodetector elements either within a single housing, the elements being separated by a narrow linear division, or separately housed, is used and the two elements are wired respectively to the + and − input ports of a differential amplifier, in the "common mode rejection" configuration. In this invention, the light from the fiber's output end illuminates the two halves of the split detector about evenly. Advantageously, the detector is positioned somewhat distant from the fiber so that about 33-100%, preferably 45-83% and optimally 60-70% of the speckles illuminate the elements of the split detector. Thus, not only is modal noise current generated due to interchange of intensity between speckle cells which fall on one or other element of the split detector and those speckle cells which miss both photodetector elements, but noise current is also generated due to interchange of intensity between speckles on one element of the split detector and speckles on the other. In fact, as will be appreciated by one skilled in the art, such interchanges are doubly effective in generating noise current because of the differential connection of the elements which serves to double the resultant noise fluctuations in the differentially summed output current due to such interchanges.

It will be further appreciated that, while this embodiment of the invention provides a novel enhancement of the modal noise sensitivity due to the interchange of speckle cell intensity between differentially connected segments of a split detector, it will also be clear to one skilled in the art that this invention also provides the well-known advantages of common mode rejection, namely, rejection of the effects of any voltage ripple present on the bias voltages provided to the two detector segments, and rejection of any AC modulated room light which might reach the detector segments. Because of the differential connection of the two segments, any such undesired photocurrents would tend to be cancelled in the differentially summed output current.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
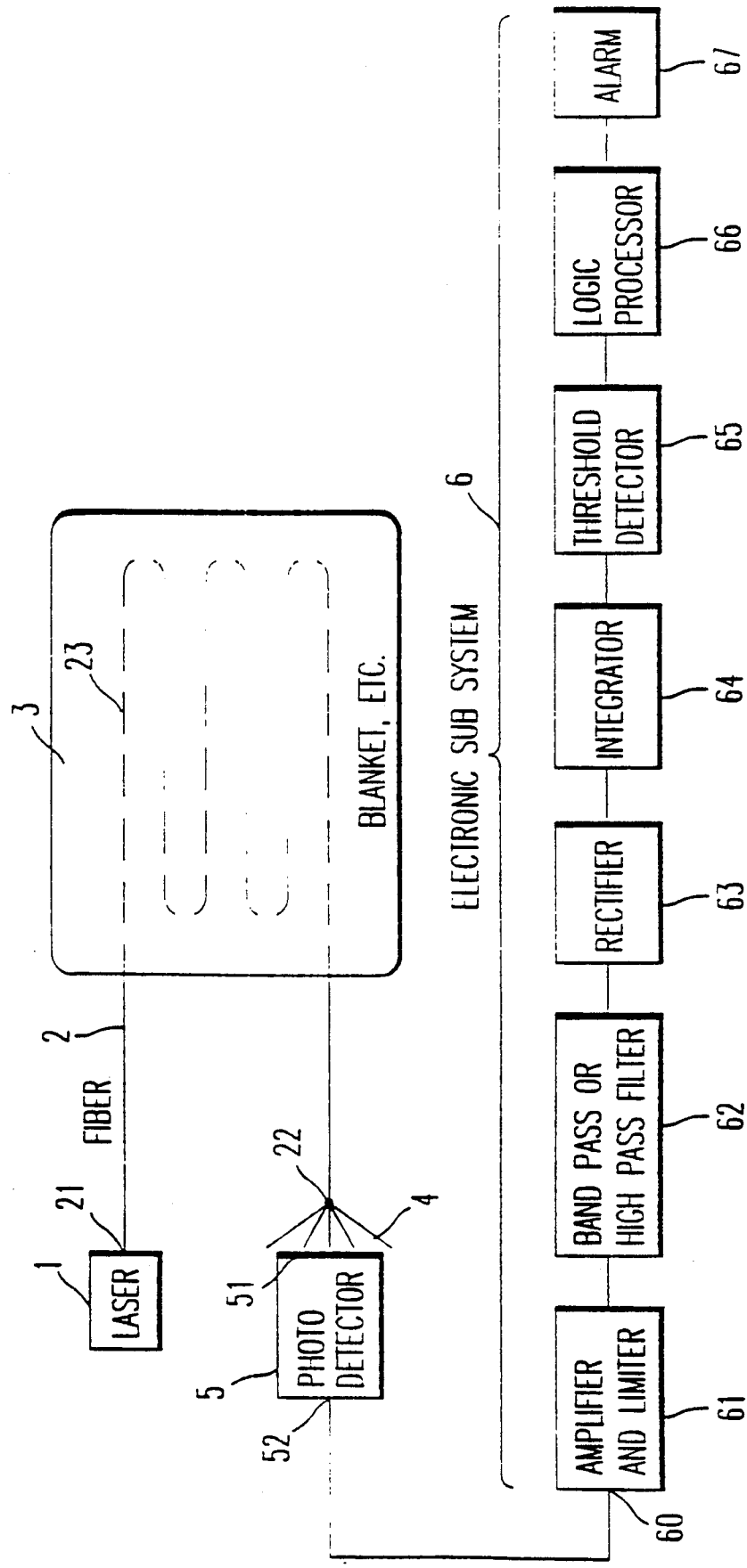
FIG. 1 is a simplified functional diagram of an apnea alarm and heartbeat monitor system according to the present invention.
Figure 2:
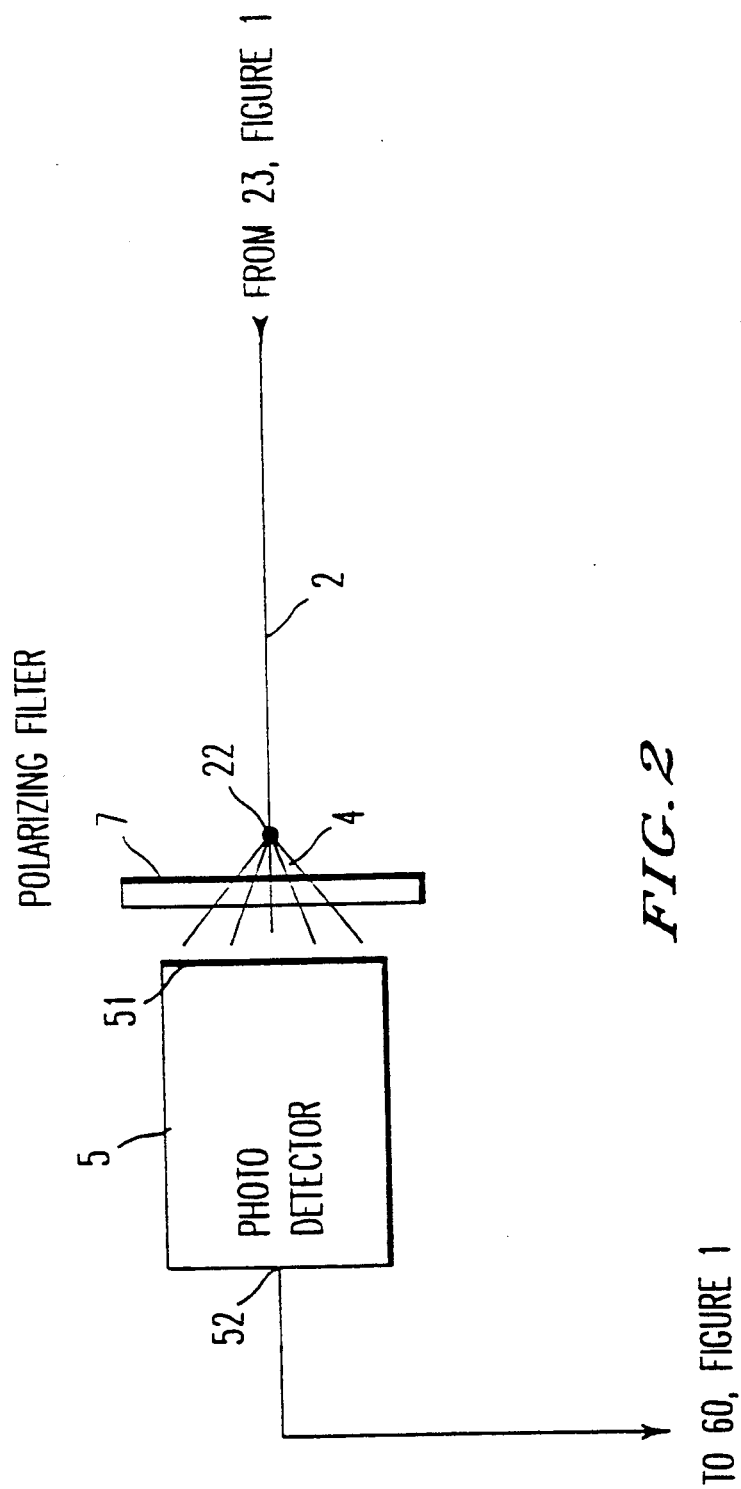
FIG. 2 is a fragmentary schematic diagram of an alternative fiber/photodetector interface for the system shown in FIG. 1.

Referring now to the drawings, wherein like reference numerals designate identical or corresponding parts throughout the several views, FIG. 1 shows a breathing and heartbeat monitor and alarm system in accordance with the current invention. A suitable coherent light source 1, advantageously a single-frequency GaAlAs injection laser diode, is driven by a continuous electrical current that is supplied by a conventional current source (not shown). Laser 1 is positioned relative to one end 21 of a multimode fiber 2 so that the light emitted by laser 1 is efficiently coupled into the fiber 2. Fiber 2 is conveniently about a few meters to a few tens of meters in length; a suitable fiber, for example, would be a plastic fiber similar to the 250 micron core, step-index, "ESKA" plastic fiber manufactured by Mitsubishi Cable America, Inc., 520 Madison Ave., New York, N.Y. 10022. Fiber 2 is woven into or otherwise mechanically coupled to a mat or blanket 3 or other item of bed clothes or sleep wear to provide a motion sensitive mechanical interface between the fiber 2 and the object or subject being monitored (not shown). The output end 22 of fiber 2 emits a cone of laser light 4, all or part of which illuminates the photosensitive plane 51 of photodetector 5, conveniently a silicon PIN detector located at an appropriate distance which provides a strong modal noise current at the output 52 of detector 5. This output noise current signal is passed to the input 60 of an electronic alarm system 6. A speckle pattern of laser light will exist in the plane 51, and detector 5 will advantageously intercept approximately half the speckle cells of that pattern.

As is known to those skilled in the art, such speckle patterns are found to be composed of many randomly shaped and positioned bright spots separated by randomly shaped dark regions. When the mid section 23 of fiber 2 is moved mechanically, the speckle pattern in plane 51 changes rapidly to one that is uncorrelated to the initial pattern. This is because the speckle pattern in plane 51 is the final result of the constructive or destructive interference among the light waves guided in each of the independent "modes," or optical paths, within fiber 2 along which laser light from source 1 is guided. Moving fiber 2 changes many or all of those path lengths minutely, or causes waves guided in one mode to be coupled into another mode, with a resulting change in optical path length. Such changes of path length need average only a fraction of a wavelength of light (i.e., about 0.4 micrometer) to substantially or totally alter the resulting speckle pattern in plane 51. Fiber bending motions of a few hundredths of a mm are sufficient to cause optical path shifts of this magnitude.

As is well known to those skilled in the art, in the case of a step-index fiber, the individual bright speckles in the detector plane are all of approximately the same average size which, in turn, is given by $a\lambda/\theta_f$, where $\lambda$ is the laser wavelength and $\theta_f$ is the angle in radians subtended by the fiber core at the detector plane, and a is a numerical constant of order 1. For example, with a detector 5 mm from a fiber having a core radius 0.1 mm, $\theta_f = 2 \tan^{-1} (0.1/5.0) = 0.04$ radians. For $\lambda = 0.63$ microns (i.e., a He-Ne laser) the average speckle size $= 0.63/0.04 \approx 16$ $\mu$m, taking $a = 1$. Typically, fiber 2 has either a "step-index distribution", in which the refractive index is essentially constant across the core, or a "graded-index" distribution, in which the refractive index decreases approximately parabolically with radial distance from the fiber axis. For the step index case, the average speckle size is nearly constant across the speckle pattern in plane 51. On the other hand, for the gradient index fiber case, the average speckle size increases near the outer edge of the speckle pattern. Speckle patterns arising in fiber optic systems have been extensively studied in connection with the noise, termed "modal noise," that such effects can generate in, for example, fiber optical data links and local area computer networks. One such study is reported in "Modal noise in multimode optical fibers," by Eric G. Rawson and Joseph W. Goodman, published in Society of Photo-Optical Instrumentation Engineers (SPIE) Vol. 355, Fiber Optics: *Short-Haul and Long-Haul Measurements and Applications* (1982), pp. 37-42, and also in "Statistics of modal noise in fibers: a case of constrained speckle," by Joseph W. Goodman and Eric G. Rawson, published in Optics Letters, vol. 6, page 324, July, 1981, both of which reports are hereby incorporated by reference.

It is well known by those skilled in the science of optical speckle that the higher the coherence of the laser light source, the higher the contrast in the speckle pattern. In the scientific literature, speckle contrast C is defined by the equation $C = (I_{max} - I_{min})/(2 \cdot I_{mean})$, where $I_{max}$ and $I_{min}$ are the highest and lowest intensities observed locally within the speckle pattern and $I_{mean}$ is the mean intensity observed across an extended portion of the speckle pattern. As is well known to those skilled in the art, a perfectly coherent laser (that is, a laser emitting in a single longitudinal mode and a single transverse mode) results in a speckle pattern contrast equal to 1.0; and a relatively incoherent source (that is, a laser emitting in two or more longitudinal modes, or in two or more transverse modes, or two or more each of both classes of modes) will yield a speckle pattern with a lower contrast. The lower the speckle contrast, the lower will be the modal noise current associated with changes in the speckle pattern. Thus, as will be appreciated by one skilled in the art, a perfectly coherent laser source is preferred over a partially coherent laser in this invention because it will yield a higher modal noise current, and hence higher sensitivity to motion. However, a partially coherent laser source can be used in this invention with a corresponding reduction in sensitivity to motion.

Detection of a part, but not all, of the light emerging from the optical fiber is preferred because for a given laser light source, fiber type, fiber length, and detector sensitivity, the noise current has a maximum value when the optical detector is illuminated by a percentage of the guided modes of the optical fiber. This condition is achieved in either of two ways: positioning or masking the detector so it is exposed to half the speckle cells in the speckle pattern; or positioning the detector so it is illuminated by all speckle cells and interposing a polarizing filter between the detector and the output end of the fiber, which polarizing filter passes only one of the two orthogonal polarizations of the light emerging from the fiber. We refer to these two cases as the "spatial filter case" and the "polarizing filter case," respectively. In the spatial filter case, and for a step-index optical fiber and a single element photodetector, this means the detector optimally subtends approximately half the area of either the near field or the far field of the light emerging from the optical fiber. In the spatial filter case for a parabolic index fiber (also called a "gradient index" fiber), the speckle sizes vary across both the near- and far-field, so the optimal detection area is not in general equal to half the full field area; but the optimal area for the single detector is still that which subtends half the speckle cells. It may be noted that in the scientific literature speckle cells are sometimes termed "speckle correlation areas."

The optimum percentage of the guided modes to be passed to the optical detector has been determined experimentally. The inventors have shown theoretically that 50% is optimum when a single detector is used, and that 66.7% is optimum when a split detector and differential detection is used. This result is based on the supposition that the total light power in the speckle pattern is conserved as speckles change patterns. Consider a detector of unit area located at a minimum distance from the fiber's output end such that the area of the speckle pattern in the detector plane is A, equal to or greater than the detector area; that is, $A \geq 1$. As the detector is moved from the position where $A = 1$ to greater distances, A increases and the fraction of speckles that strike the detector is $1/A$, and the fraction that miss the detector is $(A-1)/A$. This follows from the fact that the average speckle size is constant over the speckle pattern in a step-index fiber. A speckle intensity interchange will generate noise if one cell of the interchange falls on the detector and the other does not. Thus the probability of a noisy interchange is the product of the above probabilities: $1/A \times (A-1)/A$. Since the rate at which speckles scintillate is proportional to the fiber velocity in the sensor region, so too is the noise current: Noise $\propto 1/A \times (A-1)/A$. Setting the differential $d[\text{Noise}]/dA = 0$ to find the value of A where Noise is maximum, we find $A = 2$; that is, noise is maximum when the detector intercepts exactly half the speckle cells. Similarly, when a split detector is used, as discussed in more detail hereinafter, with differential detection, the above noise process is supplemented with noise due to interchange of intensity between the two elements of the detector. Since each element has area $= \frac{1}{2}$, the fraction of cells on each element is $1/(2A)$, and the probability that an exchange will involve one cell from each element is $1/(2A) \times 1/(2A)$, or $1/(4A^2)$. Adding this noise contribution to that already considered we get: $\text{Noise}_{split\ det} = 1/A - 3/(4A^2)$. Setting $d[N]/dA = 0$ as before, we find this noise is maximum when $A = 3/2$; that is, when the detector intercepts exactly $\frac{2}{3}$, or 66.7%, of the speckles. In this analysis we have made certain approximations. For example, as mentioned above, we have assumed that light intensity is perfectly conserved within the speckle pattern as the pattern scintillates; we know that this is not strictly true, that some energy is exchanged with radiative modes in the fiber as the fiber moves, so that there are some small fluctuations in the total speckle pattern power. Additionally, we have assumed that the average speckle pattern intensity is constant over the pattern, whereas it is known that, due to coupling of high order modes to lossy (radiating) modes, the intensity is normally lower near the outer edges of the pattern than elsewhere. Because of these approximations we would anticipate that the above analysis, although not exactly predictive of the A values for maximum noise signals in all cases, gives close approximations of the true values in all cases of interest.

Figure 3A:
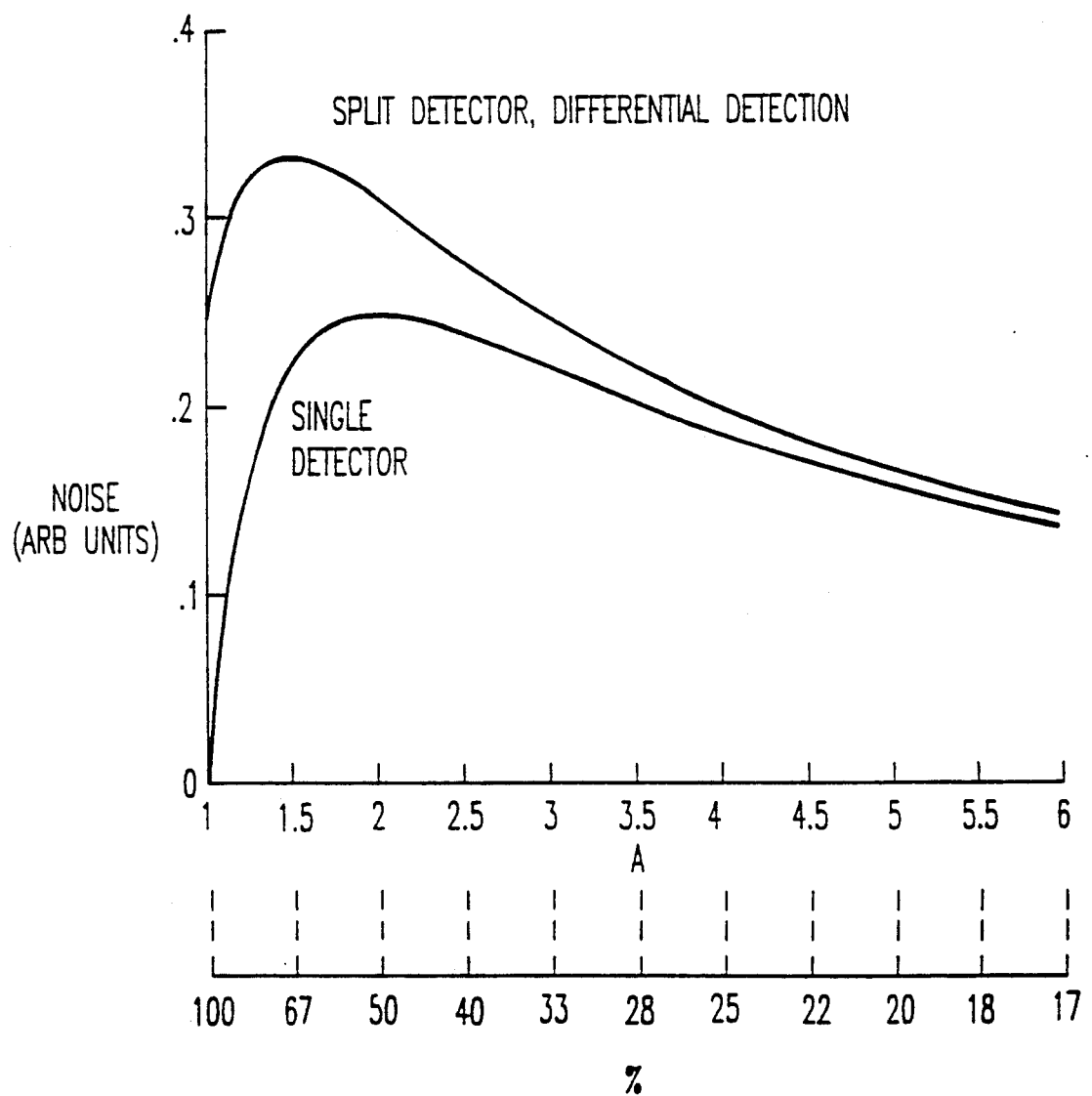
FIG. 3a is a graph illustrating a theoretical relationship between modal noise and speckle pattern area.

FIG. 3a plots noise vs speckle pattern area A, assuming a detector area of unity and $A>1$, for the single detector case and the split detector, differential detection case, using the equations derived above. It can be seen that the corresponding A values for maximum noise are as derived above, namely $A=2.0$ and 1.5, corresponding to speckle fractions on the single detector of 50% and on the split detector of 66.7%.

The curves shown in FIG. 3a are useful to assist in determining the optimum percentage or range of percentage of speckle cells to be intercepted by the single detector and the split detector detection configurations. FIG. 3a indicates that 50% detection is optimum for the single detector and 67% is optimum for the split detector. A preferred range configuration is where the noise is greater than 0.2 (arbitrary units), i.e., 27–74% for the single detector and 24–100% for the split detector, with an even more preferred range for the split detector being where noise is greater than 2.5 (33–100%), particularly where noise is greater than 3.0 (45–83%) and optimally in the 60–70% detection range.

The relationship between modal noise level and the fraction of speckle cells illuminating the photodetector was investigated by the inventors by means of an experiment in which a He—Ne laser illuminated a 4 m long plastic fiber with a 250 μm core and a numerical aperture (NA) of 0.5. Connectors were placed on each end of the fiber and the laser illuminated the fiber input end without intervening optics. The fiber was loosely wrapped about a foam plastic cylinder of about 10 cm diameter which in turn rested on a soft blanket. A small DC motor was positioned so that it rested in contact with several loops of the fiber about the foam cylinder. When this motor was running it provided a constant and reproducible level of mechanical vibration to the fiber. The final meter of fiber ran to a connector socket which positioned the fiber (cemented in its output connector) to illuminate a 1 cm diameter PIN photodetector positioned a few mm away, this distance being small enough that the cone of light emerging from the fiber underfilled the 1 cm diameter of the detector.

The detector used had four quadrants, each with its own electrically separate output lead. The four quadrants were connected together electronically so that the detector behaved as a single homogenous detector (except for the narrow division lines between the four quadrants, an effect of which is discussed below). A knife edge was mounted on a precision translation device equipped with a vernier scale and positioned in a plane close to the plane of the detector so that advancing the translation stage moved the knife edge progressively in front of the detector, from a position where it occluded none of the laser light (the speckle pattern) to one where it occluded all of the speckle pattern. The detector was connected to an electronic amplifier in such a way that it was possible independently to measure both the total DC photocurrent due to the laser light and the modal noise due to scintillations in the speckle pattern.

Measurements were taken of the DC photocurrent and the modal noise current as a function of the knife edge position.

Figure 3B:
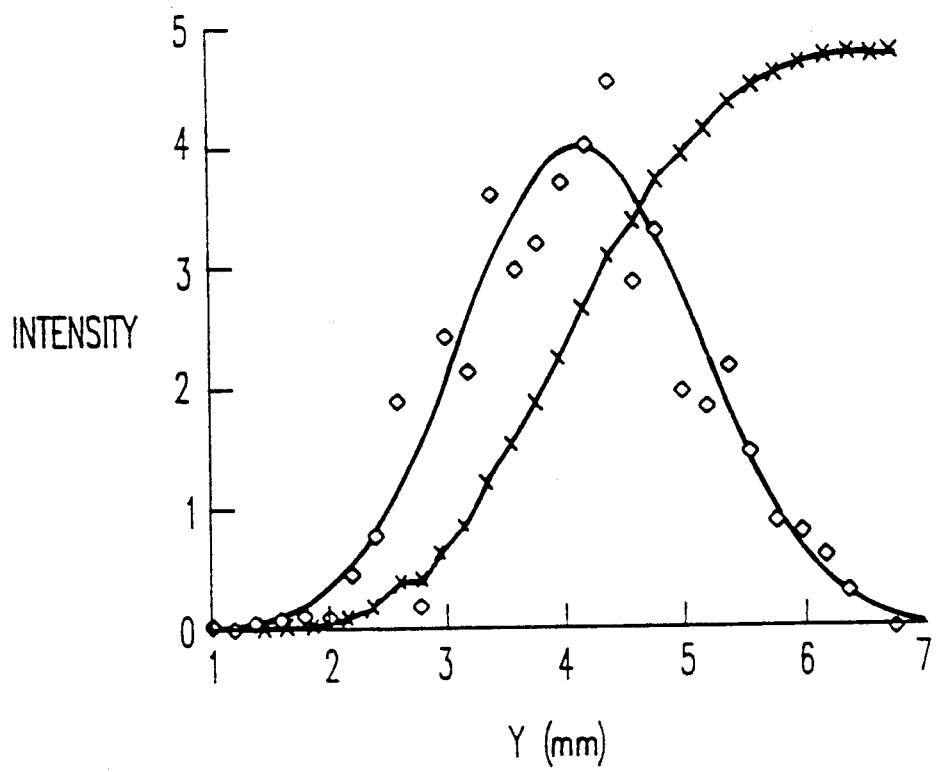
FIGS. 3b, 3c and 3d are graphs illustrating the relationship between the measured modal noise and speckle pattern area.

FIG. 3b shows the DC photocurrent, which is proportional to the light intensity falling on the detector, as an S-shaped solid line connecting data points shown as Xs, plotted as a function of Y, the knife edge position in mm. The derivative of this curve (i.e., it's slope), gives the rate of change of light intensity as a function of Y. The derivative of the S-curve is shown as the diamond shaped data points. While there is considerable scatter in the derivative points, the trend is clear; the nearby solid line shows a best-fit "gaussian", or "normal" distribution fitted to the derivative points. It can be seen that the rate of change of intensity distribution is nearly normal and peaks at about 4.2 mm on the Y scale. This distribution is useful in identifying the value of Y at which the knife edge occludes exactly half of the speckle pattern.

Figure 3C:
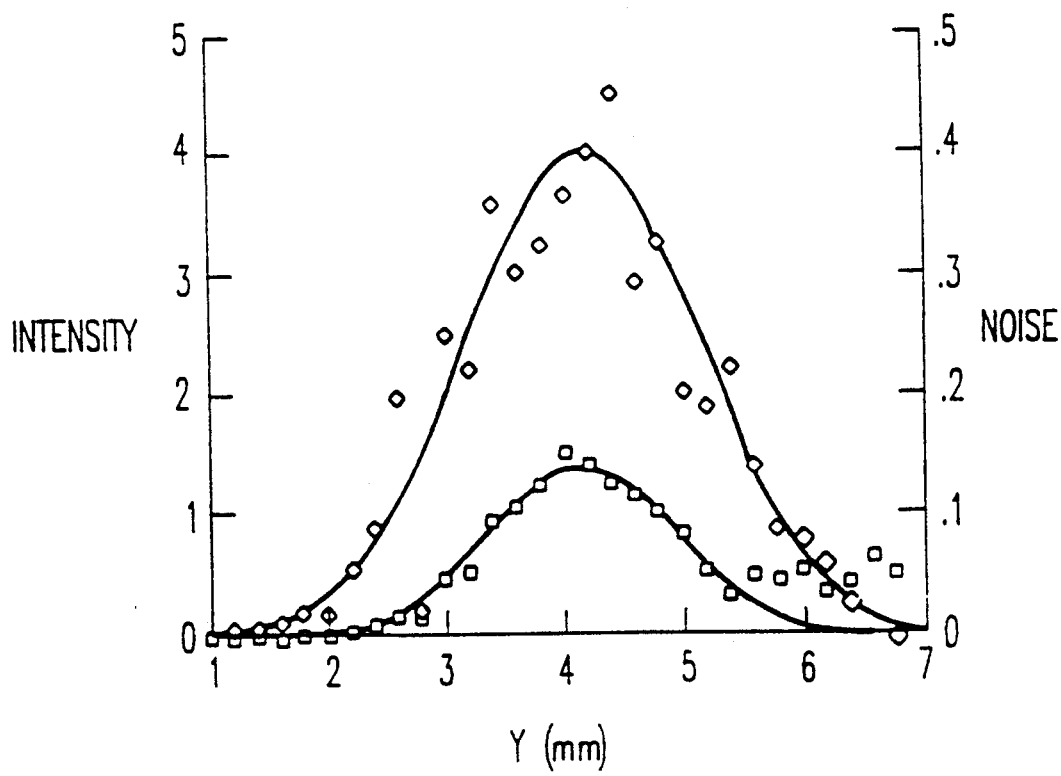

FIG. 3c shows a repeat of the derivative points and the fitted normal distribution of the rate of change of the incident light intensity, together with a plot of the corresponding modal noise average amplitude, shown as square data points. The solid line adjacent to the square data points is once again a best-fit gaussian (normal) distribution. It can be seen that the noise distribution is a maximum when the knife edge is centered in the speckle pattern; that is, when about 50% of the speckles pass the knife edge and the other 50% are blocked by the knife edge.

It is apparent that the modal noise signal does not completely go to zero when the knife edge is clear of the beam (i.e., near $Y=7$ mm). This is attributed primarily to the division lines between the four quadrants. These division lines represent areas of the detector which are insensitive to incident light, and thus represent spatial filtering. Another possible cause for the non-zero noise amplitude near $Y=7$ is scattering of speckle light by imperfections in the cleave of the fiber's output face, causing a small amount of light not to fall on the photo detector. Yet another possible cause for the non-zero amplitude near $Y=7$ is the interchange in the fiber of guided light between guided and radiative (lossy) modes. The inventors' experiments and measurements confirm that most such energy exchanges are between guided modes and so do not result in noise fluctuations of the total guided power, but it is possible that a few high-order modes are participating in such exchanges with radiative modes. Such exchanges would result in non-zero amplitudes near $Y=7$.

Figure 3D:
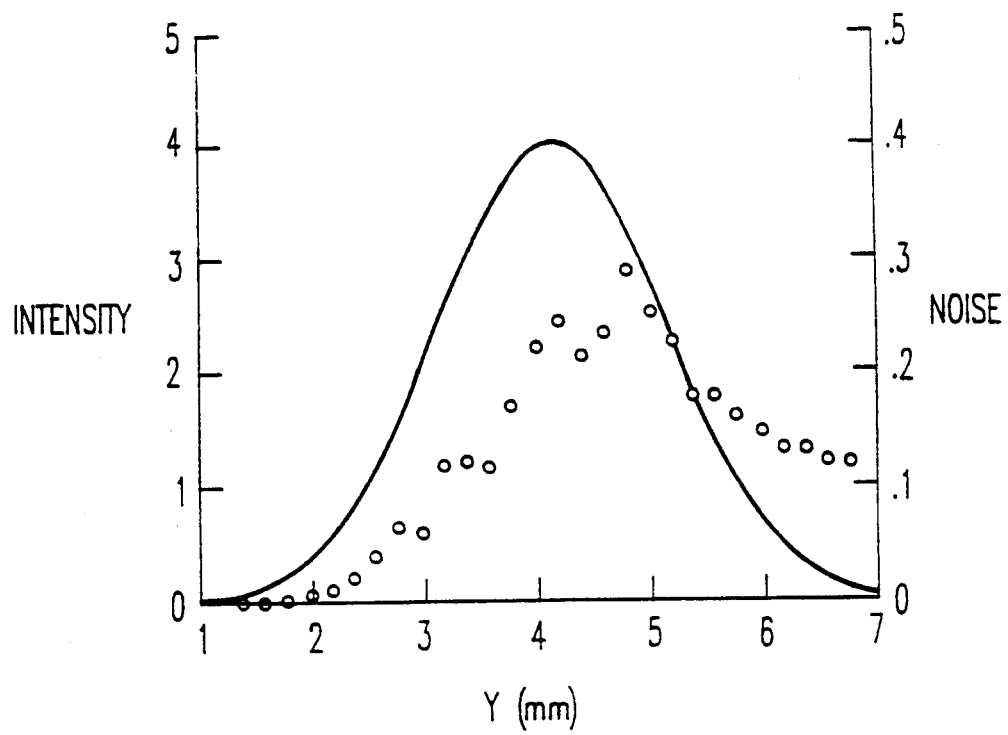
Figure 3E:
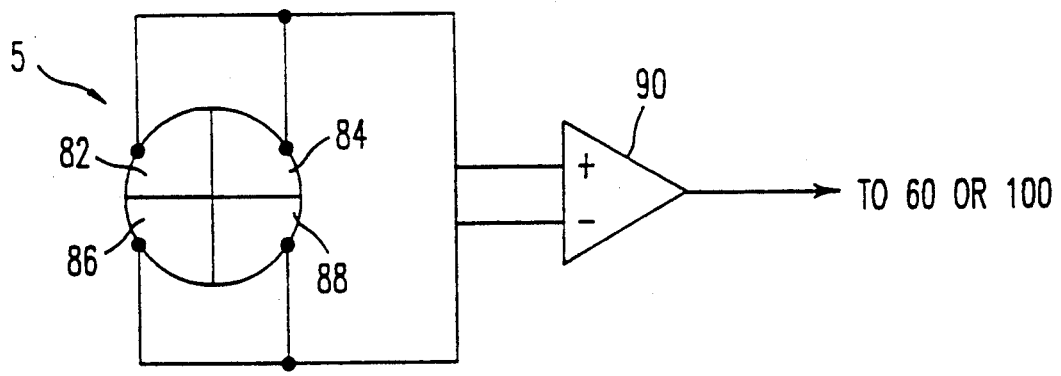
FIG. 3e is a schematic circuit diagram illustrating a differential detection circuit employed to obtain the data of FIG. 3d.

FIG. 3d shows a plot of the modal noise when the two adjacent quadrants 82, 84 are wired in parallel, and the other two quadrants 86, 88 are likewise (but independently) wired in parallel, and the photocurrents from the resulting half-circle detectors are wired to the + and − inputs of an operational amplifier 90 as shown in FIG. 3e. In this configuration the quad detector simulates a 2-segment, or "split" detector, wired for differential, or "common-mode rejection", detection. It can be seen in FIG. 3d that the modal noise peaks somewhat off-center, closer to the "fully open aperture" (i.e., $Y=7$) case, and close to the ⅔ area point derived above. Also, there is significant noise present even in the fully open aperture case, in agreement with the earlier analysis for a split detector with differential detection.

This detector configuration, commonly called "differential detection", presents the well-known virtues of "common mode rejection" (i.e., cancellation of any Hz ripple noise on the bias voltage which biases the photo detectors, and any 60 Hz room light which might reach the detectors). But more significantly in this context, and as explained earlier, it also doubles the modal noise currents due to any speckle intensity exchange between speckle correlation cells which are located on opposite halves of the detector. That is, a cell whose intensity disappears on one side and reappears on the other side doubles its noise current contribution due to the two currents being differenced at the operational amplifier. Also, this effect (noise current due to intensity exchange between detector halves) occurs even in the full aperture (Y=7) case; the noise at full aperture is seen to be still about 50% of its peak value.

Thus, despite the above-discussed departure near Y=7 from the ideal distribution seen in FIG. 3c, it is clear that the modal noise distribution in FIG. 3c is essentially gaussian and that it peaks essentially at the 50% area point, in accordance with the teachings of the parent patent application Ser. No. 07/802,868.

Differential detection using a split detector of separate detectors significantly improves the sensitivity of modal noise detection, and thus offers an improvement over single detector detection.

From the above discussion, it is clear that this invention is not limited to the use of a detector that is illuminated by approximately half the speckle cells (or ⅔ in the case of a split detector and differential detection), as described above, nor is it necessary to use a polarizing filter to limit the number of guided modes illuminating the detector. Detection of more or less than half of the output light from the fiber (or ⅔ for the split detector, differential detection case) will still result in a functioning system, but one with a smaller average noise current. In particular, the detector can be illuminated by essentially all the light emerging from the optical fiber; however, the modal noise associated with this case will be significantly less than when approximately half of the emerging light is detected, as is evident from FIG. 3c, or less than when approximately ⅔ of the emerging light is detected, as is evident from FIG. 3d, in the split detector, differential detection case.

More particularly, the modal noise modulation mechanism in the case where essentially all the light emerging from the optical fiber illuminates the detector can be understood as follows. Some light, which a moment before was guided in certain high-order guided modes (i.e., modes propagating at such large angles to the fiber axis that they are close to the radiative "cut-off" angle), may be switched into non-guided (radiative) modes (i.e., modes propagating at angles exceeding the cut-off angle) when the fiber moves, contributing to a reduction in the total guided optical power. Similarly, fiber motion may cause some light, which a moment before was being coupled into radiative modes (and thus being lost from the fiber), to be switched back into guided modes, contributing to an increase in the total guided optical power. Thus, modal noise current fluctuations are generated when the fiber moves, even in the case where the detector is illuminated by all the guided modes. While the RMS amplitude of the noise current in the full-field detection case is less than that of the half-field detection case, or less than that of the ⅔ detection case when using a split detector and differential detection, the simplicity of full-field detection may make it a useful option despite this reduced sensitivity to motion.

In order to compare the noise efficiency of various ways of reducing the fraction of detected speckle cells and in order to determine the optimum fraction of detected speckle cells, the inventors have performed various experiments, some of which are discussed above, and which are further discussed hereinafter.

Experimental measurements comparing the noise efficiency of four ways of reducing the fraction of speckle cells illuminating a single detector to 50% were performed. The four methods were: use of a knife edge to block half the beam; use of a 50% Ronchi ruling screen in front of the detector; use of a polarizer in front of a detector which blocks one of the two orthogonal polarizations; and separating the end of the waveguide from the photodetector by sufficient distance so that only 50% of the light emitted from the optical waveguide is incident on the photodetector. It was experimentally verified that in all four types of filtering using a single detector, no difference in modal noise amplitude was observed within the accuracy of the measurements. It was also experimentally verified that full-field detection utilizing a single detector resulted in a reduced amount of modal noise, to approximately 20% of that realized with 50% filtering. This reduced modal noise, to 20%, for full-field detection confirms that full-field detection may be an option under certain circumstances.

The results of the measurements performed by the inventors have led the inventors to conclude that the speckle energy exchange is a sufficiently "long-distance" effect, (here we are referring to the distance, across the speckle pattern, between the two speckle correlation cells that are exchanging optical power) such that there is no measurable sensitivity advantage to subdividing the blocked area into smaller regions with a ruled or checkered screen beyond that achieved with a single knife edge, or by separating the fiber end from the detector so that 50% of the light falls on the detector. The inventors have concluded that blocking half the cells with a polarizing screen offers no advantage in its noise efficiency over blocking half the cells with a knife edge or other 50% spatial filtration means in the case of a single detector, such as a screen, or simply locating a circular detector at a distance such that it subtends half the Figure's emission cone solid angle.

Experiments performed by the inventors experimentally verified that 50% was the optimal spatial filtering fraction when a single detector was used. Additional experimentation showed that the use of a split detector and differential detection increased sensitivity by a factor of about 2× and shifted the optimal fraction upward to about ⅔ of the speckle pattern.

In experiments performed to compare polarization- and spatial-filtration in the case of differential (two-detector) detection, it was determined that cross polarizer differential detection with two detectors and a conventional (non-polarizing) prism beam splitter is almost as sensitive as the same system with two 50% Ronchi Rulings in place of the polarizers, about as sensitive as the use of single polarizer in front of a single detector, and almost as sensitive as a 50% Ronchi Ruling or 50% knife-edge on a single detector with no prism. Thus, based on experiments performed by the inventors, it has been concluded that polarization filtration offers no advantage over simpler spatial filtration, either with a single detector, or with a split detector or separate detectors performing differential detection. When it is considered that inexpensive readily available polarizer material is somewhat absorbing, introducing a small (about 20%) signal penalty, filtration using polarizers is further disadvantaged.

Figure 4A:
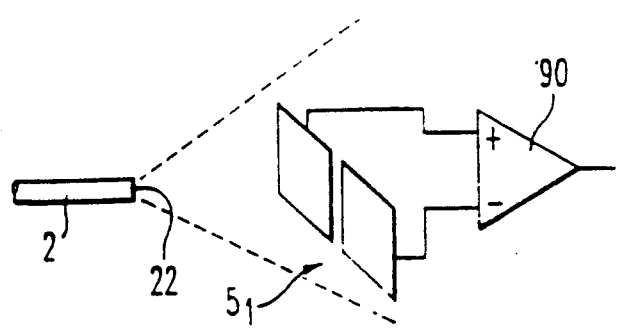
FIGS. 4a, 4b, 4c, 4d, 4e, 4f, 4g, 4h, 4i and 4j are schematic sketches of different detection circuits which can be employed according to the present invention.
Figure 4B:
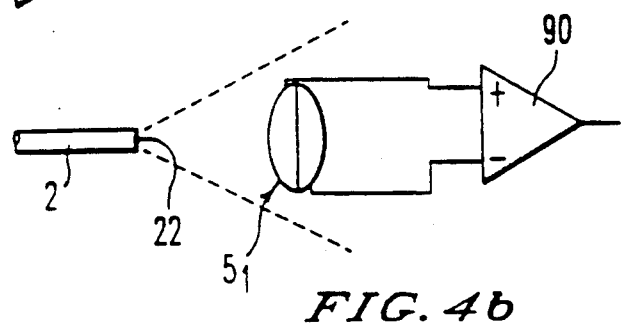
Figure 4C:
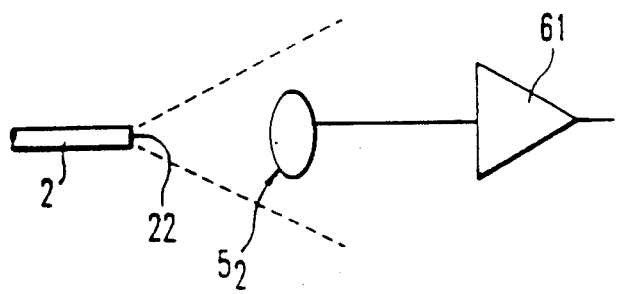

In view of the experimental results obtained by the inventors, a preferred embodiment of a detection system used in the present invention employs a two-element PIN photodetector $5_1$, a split detector with either rectangular elements as shown in FIG. 4a or hemicircular elements as shown in FIG. 4b, differentially connected to a differential amplifier 90 to provide common mode rejection and a doubling of the portion of the noise current due to intensity exchange between the photodetector elements, wherein the photodetector elements are positioned some distance away from the fiber output and so that they intercept a 33-100% fraction, preferably 45-83%, and optimally 60-70% of the speckle correlation cells. Correspondingly, if a single detector $5_2$ is used, as shown in FIG. 4c, a preferred embodiment of the single detection system places the photodetector spaced apart from the fiber output end 22 so that it likewise intercepts an optimal fraction, for example, 27-74% and optimally approximately 50%, of the speckle correlation cells.

Figure 4D:
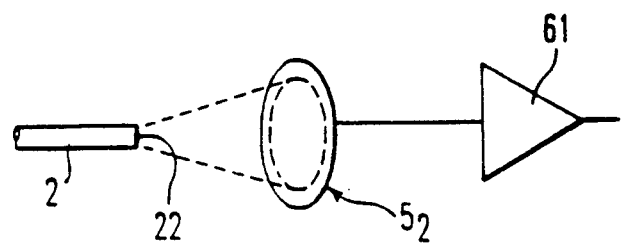
Figure 4E:
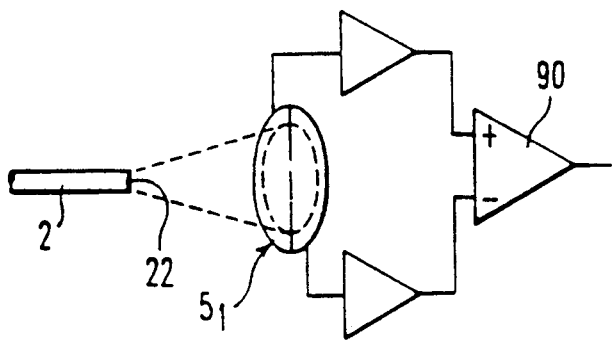

In addition to the preferred embodiments of the detection system above described, many different variations are also possible. For example, in a variation of the single detector system, the photodetector $5_2$ is positioned to collect all of the modal light from the output of the fiber, as shown in FIG. 4d. This technique is inefficient because it relies on exchange of the light between a guided and unguided modes, a weak effect, and may have an efficiency of 5 to 20% of that of the preferred embodiments. Similarly, a split detector $5_1$, with differential detection detecting essentially all of the light on the two approximately equal photodetectors is also possible, as shown in FIG. 4e, but not as efficient as the preferred split detector embodiment. Further, the shapes of the detectors for either the split or the single detector embodiments does not affect performance. Separate rectangular, circular, or other-shaped photodetectors having about equal areas, or similar such split detectors, are equally effective.

Figure 4F:
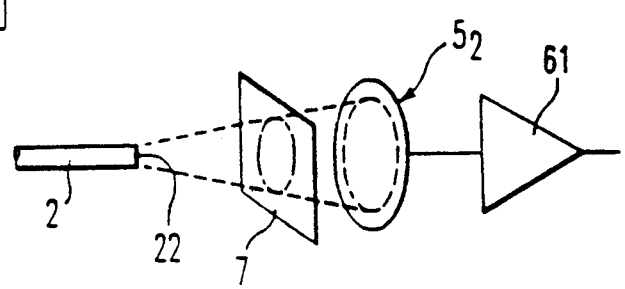
Figure 4G:
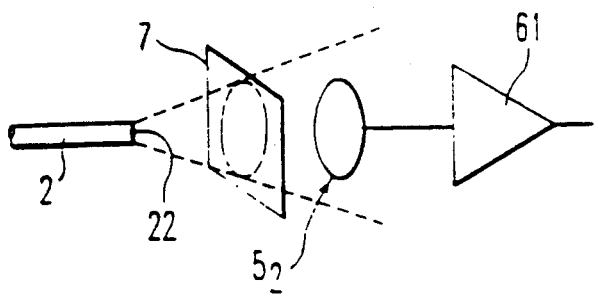
Figure 4H:
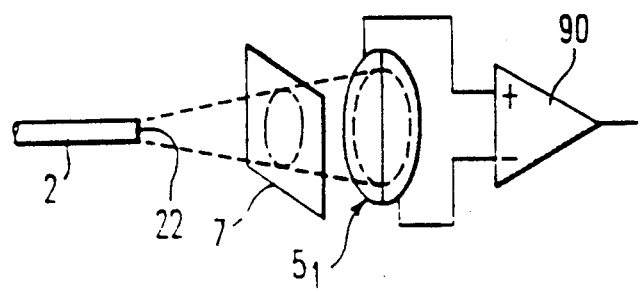
Figure 4I:
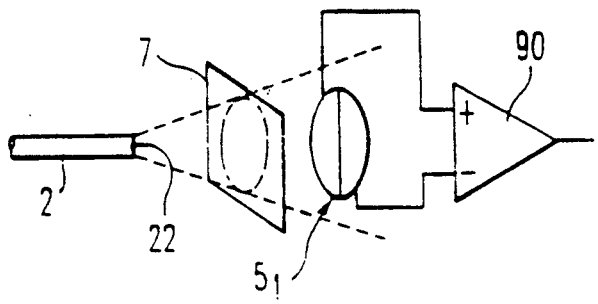

Similarly, as in the spatial filtering embodiment, the polarization filtration embodiment is also usable even if all the light which passes through the polarizer 7 is intercepted by the photodetector, as shown in FIG. 4f. This is a less efficient approach than either of the preferred embodiments, for the reasons above noted. Even less efficient would be a small single detector $5_2$ which detects only part of the light passed through a polarizer 7, as shown in FIG. 4g, which generates noise in two ways, including an exchange between polarizations and an exchange with cells which miss the detector, because the combination reduces the percent of speckle striking the detector to less than the optimal 50%. Likewise, where a differential detector $5_1$ is employed in conjunction with a polarizer 7, as shown in FIG. 4h, noise is generated in two ways, firstly by exchange between the polarities, and secondly by exchange between the halves of the photodetector $5_1$ due to differential detection. Efficiency is unnecessarily low because the polarizer reduces the modes to 50%, below the optimal 66.7%, and also because the polarizer attenuates the light by about 20%. Where the photodetector $5_1$ is arranged to intercept only a part of the light passing through the polarizer 7, as shown in FIG. 4i, and where differential detection is employed, noise is generated in three ways, including exchange between the different polarizations, exchange between halves of the photodetector cells (differential detection), and exchange with cells which miss the detector; but the efficiency is again less than in either of the preferred embodiments because the combination of filtration methods over restricts the percentage of modes illuminating the detector.

Figure 4J:
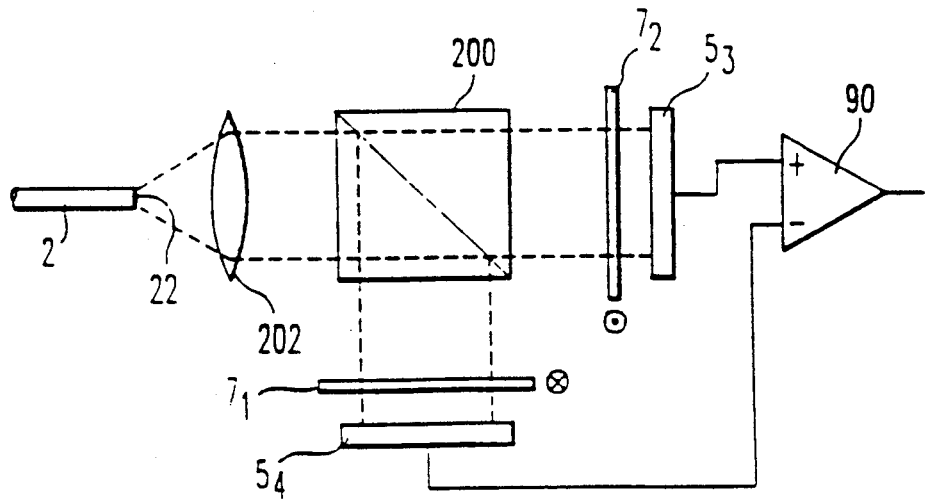

In yet another embodiment involving polarization filtration, as shown in FIG. 4j, use can be made of beam splitter prism 200 to split light from the output 22 of the fiber 2 into two paths. In this embodiment, a collimator lens 202, e.g., a $\mu$-scope objective lens with a sufficiently large numerical aperture to not vignette the beam of light from the fiber, is introduced between the fiber optic end 22 and a nominally 50%-50% beam splitter prism 200 which splits the collimated light into two different beams of essentially equal power. Each path includes a polarizing filter, $7_1$ or $7_2$, the polarizations of which are crossed in orientation so that one filter passes light with on polarization orientation and the other passes light with the other polarization orientation, and light passing through the two polarizers impinges on respective photodetectors $5_3$, $5_4$ which are connected to a differential amplifier 90 for differential detection of the signals produced by the two detectors $5_3$, $5_4$. Thus, energy exchange between polarizations will give rise to substantial noise currents in the differentially detected output signal. This system is somewhat complex, and is therefor costly.

In another embodiment (not shown), the polarizing filters and ordinary beam-splitting prism of the embodiment above discussed are replaced with a polarization beam-splitting prism which provides both splitting and polarization of the collimated light from the output of the fiber. Such a prism works marginally better than the use of separate polarizers because the polarization prism avoids the typically 20% attenuation loss of common polarizing filters, so that the signal applied to the photodetectors is 20% larger. But the cost of such polarizing prisms is relatively high. Also, there is additional cost associated with the objective lens for collimation, and two detectors may be more expensive than one detector, whether single or split, as used in the preferred embodiments From the above discussion, it is believed clear that various combinations of detection embodiments are possible. For example, a splitting prism can be used in combination with spatial filtering instead of polarization filtering, using any of the spatial filters above discussed. For example, a Ronchi Ruling or knife edge or other similar implement can be introduced between a fiber optic end and a detector positioned to detect all or only part of the light passed. The photodetector can either be a single photodetector or a split photodetector, or separate photodetectors, with the amount of light being received by the photodetector(s) preferably being optimized to maximize modal noise. Once again, however, it is emphasized that operation is possible at less than maximum modal noise production.

As will be appreciated by one skilled in the art, the speckle pattern is essentially an optical interferometric effect. Thus, it is to be understood that optical interferometric measurement of mechanical movement is a highly sensitive process, ultimately able to detect movements on the order of a wavelength of light (about 0.6 micro meters for coherent light from a Helium—Neon laser). For this reason the sensitivity of this invention in detecting small motion amplitudes is significantly higher than with prior art techniques.

While there are different ways in which the output modal noise current signal could be electronically processed to derive a suitable apnea alarm signal, one embodiment is illustrated in FIG. 1. As shown, the electronic alarm system 6 is comprised typically of an amplifier and limiter 61 which amplifies the noise current and limits its amplitude, while preserving its frequency content. As is well known to those skilled in the electronics arts, the amplifier may require automatic gain control and AC coupling to accomplish this effectively. The output of amplifier/limiter 61 is passed through a band-pass or high-pass electronic filter 62 which selectively passes the high frequency components of particular relevance in apnea detection. This filtered AC signal then is applied to a rectifier circuit 63 which derives a DC output signal whose amplitude is proportional to the amplitude of the filtered AC signal. The rectified signal, in turn, is passed to an integrator 64 which integrates the rectified signal for a suitable time which is of the order of a fraction of a normal breath period (that is, this integration time constant might be about 1-2 seconds). These parameters are adjusted to selectively maximize the signals attributable to fiber velocities during normal breathing. A threshold detector 65 monitors the output of the integrator 64 to signal a logic processor 66 when a normal breath event is sensed. This enables the logic processor 66 to trigger an alarm 67 if normal breathing ceases for a sustained period (which might be about 15 seconds), or if breathing occurs with abnormally high frequency for a sustained period (which might be about one minute). The latter condition would be an indication of distressed breathing which, as mentioned above, the present invention is also able to detect and report. Similarly, normal heartbeat patterns can be distinguished from abnormal patterns; in particular, normal heart rates can be distinguished from abnormal heart rates, and cardiac arrhythmia patterns can be detected.

Figure 5:
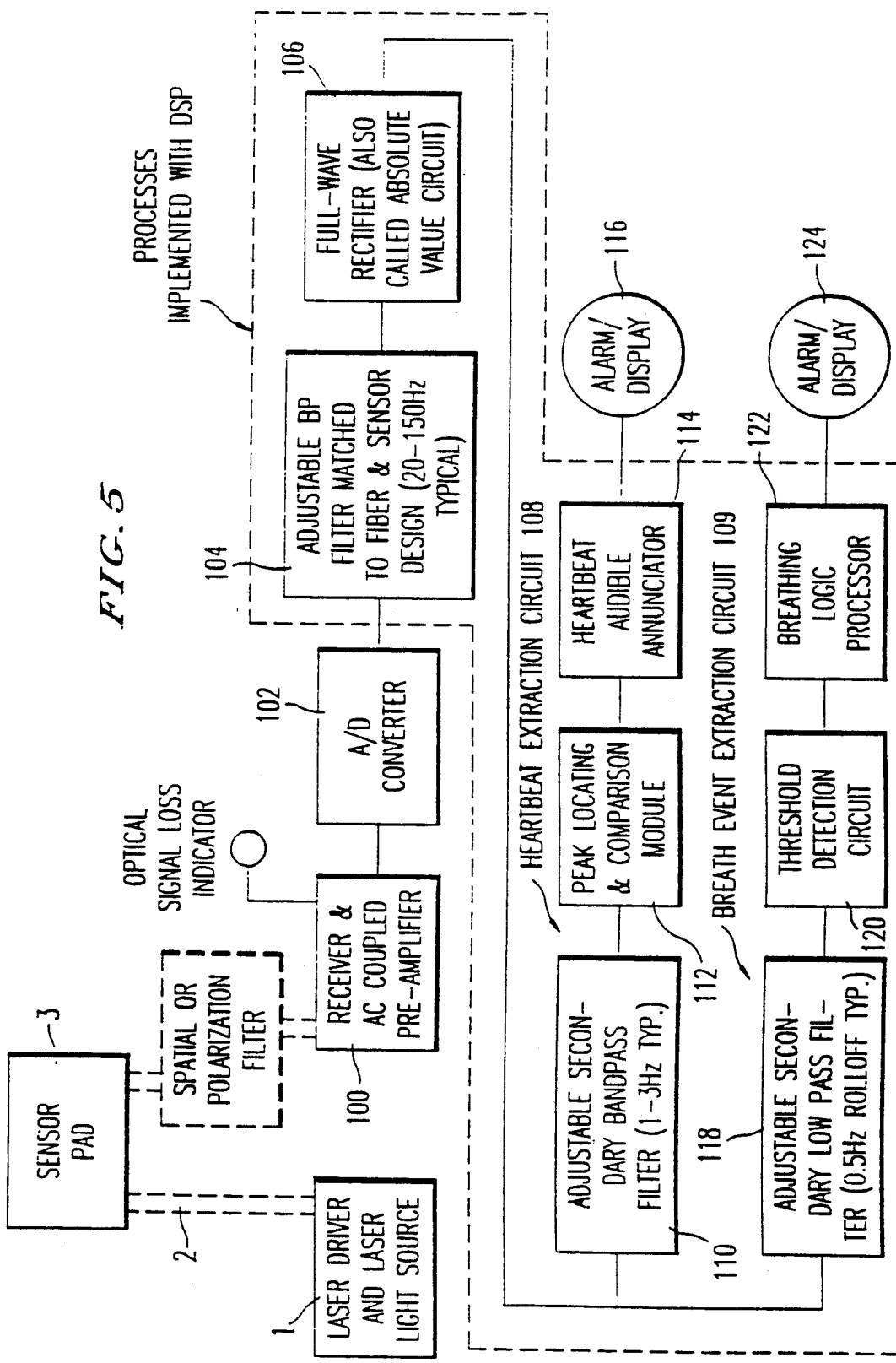
FIG. 5 is a simplified functional block diagram of an improved breathing and heart monitor system of the present invention.

FIG. 5 is a schematic block diagram of another embodiment of the invention. In this embodiment, the filtered output of the sensor pad is filtered either spatially or polarmetrically by means of a filter shown in phanthom, or is positioned away from the detector so that the detector intercepts a predetermined percentage of the speckles of light at the output of the detector, and is then applied to a detector/receiver and AC coupled pre-amp circuit 100 which outputs a visual signal indicative of optical signal loss and an analog voltage signal indicative of the noise current. The analog output signal of circuit 100 is applied to A/D converter 102, which produces a digital output applied to a digital signal processor (DSP). The DSP performs several functions illustrated schematically in FIG. 5, which is next described in a circuitry context, although in the preferred implementation the DSP functions are implemented in software. First, the digital signal is applied to an adjustable bandpass filter 104 having a passband matched to the particular design of the sensor pad. For one such design above-discussed, the passband was in the range of 23-200 Hz, and was preferably 33-133 Hz, where most of the energy relating to breathing and heartbeats was found. For a given sensor pad design, the upper and lower cutoff frequencies of the filter 104 are adjustable by a factor of ±2 or so. The output of filter 104 is full wave rectified by rectifier 106. The rectifier 106 applies a rectified output signal to a heartbeat extraction circuit 108 and to a breath event extraction circuit 109 which respectively detect heartbeat and breathing events.

Heartbeat extraction circuit 108 includes adjustable secondary bandpass filter 110 having a passband of ~1-3 Hz in which the edge frequencies are independently adjustable higher and lower in frequency by up to a factor of two; peak location and comparison circuit 112; and processor 114 which takes the output of circuit 112, determines the heartbeat rate, and triggers an alarm 116 if the heartbeat rate is outside a predetermined range, or changes at a rate of change outside a predetermined range. The passband of the filter 110 may be manually adjusted, or automatically controlled by an AI (artificial intelligence) circuit, neural network, so-called "fuzzy logic", or other processor.

Figure 6:
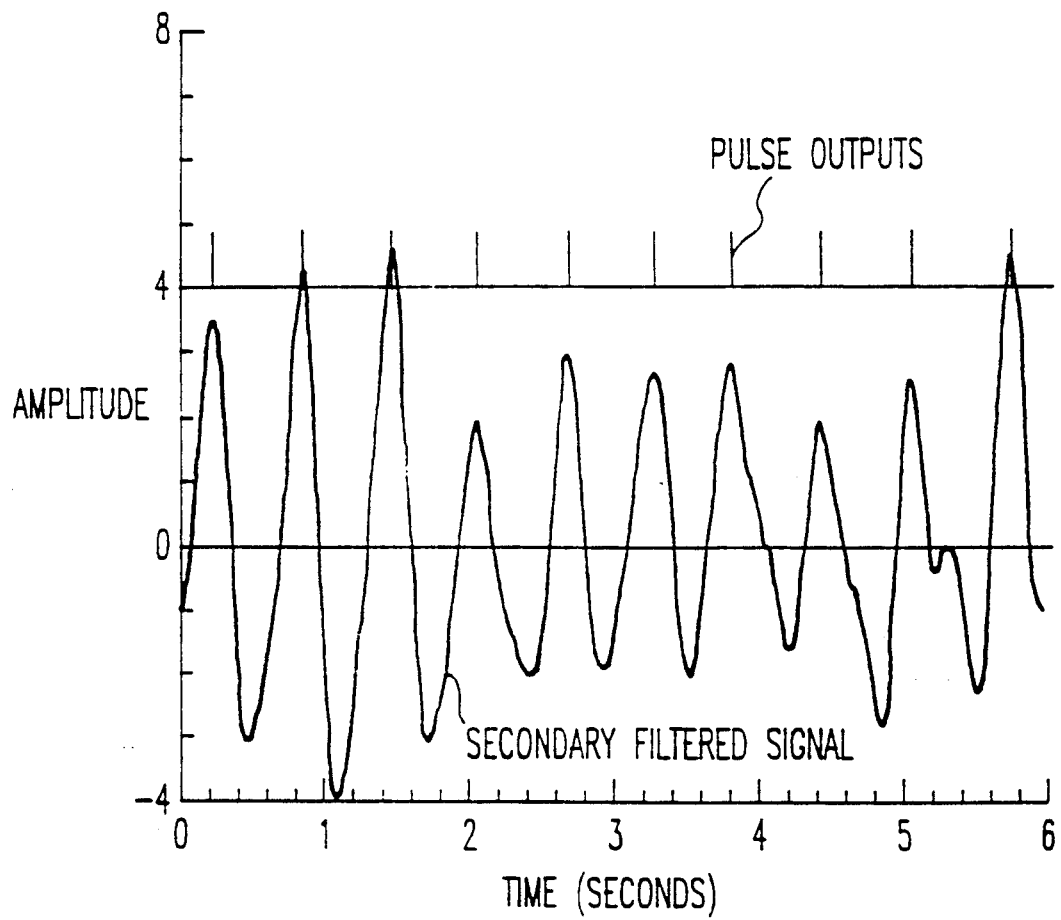
FIG. 6 is a graph illustrating detected heartbeat signals, as achieved by the heartbeat extraction circuit shown in FIG. 5.

The circuit 112 performs a peak detection method which can be summarized as follows. Whenever the data curve rises above the zero-line, the maximum height the curve reaches before returning below the zero line is noted. If this maximum height meets or exceeds a sufficient height, as defined below, a heartbeat is declared. The time of the heartbeat can be approximated either as the moment when the data curve reaches its maximum height, or, more conveniently in practical applications, as that moment when the data curve recrosses the zero-line after having reached the aforementioned sufficient height. An electronic record is kept of the ten most recent pulse heights whether or not the data curve reached the aforementioned sufficient height, and the average of those ten is taken. To be counted as a heartbeat, a data curve which rises above the zero line must exceed a predetermined fraction, normally 25%, of that average. Until ten pulses have occurred, the first pulse is counted multiple times to make up the equivalent of ten pulses. If a pulse has multiple peaks before returning to zero, the highest peak is evaluated, as noted above. FIG. 6 shows the waveform of the rectified, integrated, and secondary filtered signal as it emerges from the secondary filter 110 of circuit 108 and is applied to the circuit 112 (middle of FIG. 6), and the pulse outputs of the circuit 112, indicating presence of heartbeats, applied to the processor 114.

The breathing extraction circuit 109 is constructed similar to the heartbeat extraction circuit 108, but with important differences. Circuit 109 includes an adjustable secondary low-pass filter 118 having a cutoff frequency in the range between 0.2 and 0.5 Hz, which is adjustable by a factor ~2x (such adjustments noted here and elsewhere permit the monitor to be adapted to subjects of differing body weights and positions) and which in conjunction with the full wave rectifier 106 performs an envelope detection function; and adaptive threshold detector circuit 120 discussed hereinafter, and a logic processor 122 performing the same functions as that of the logic processor 114. The logic processor 122 applies an output to alarm/display 124.

Figure 7:
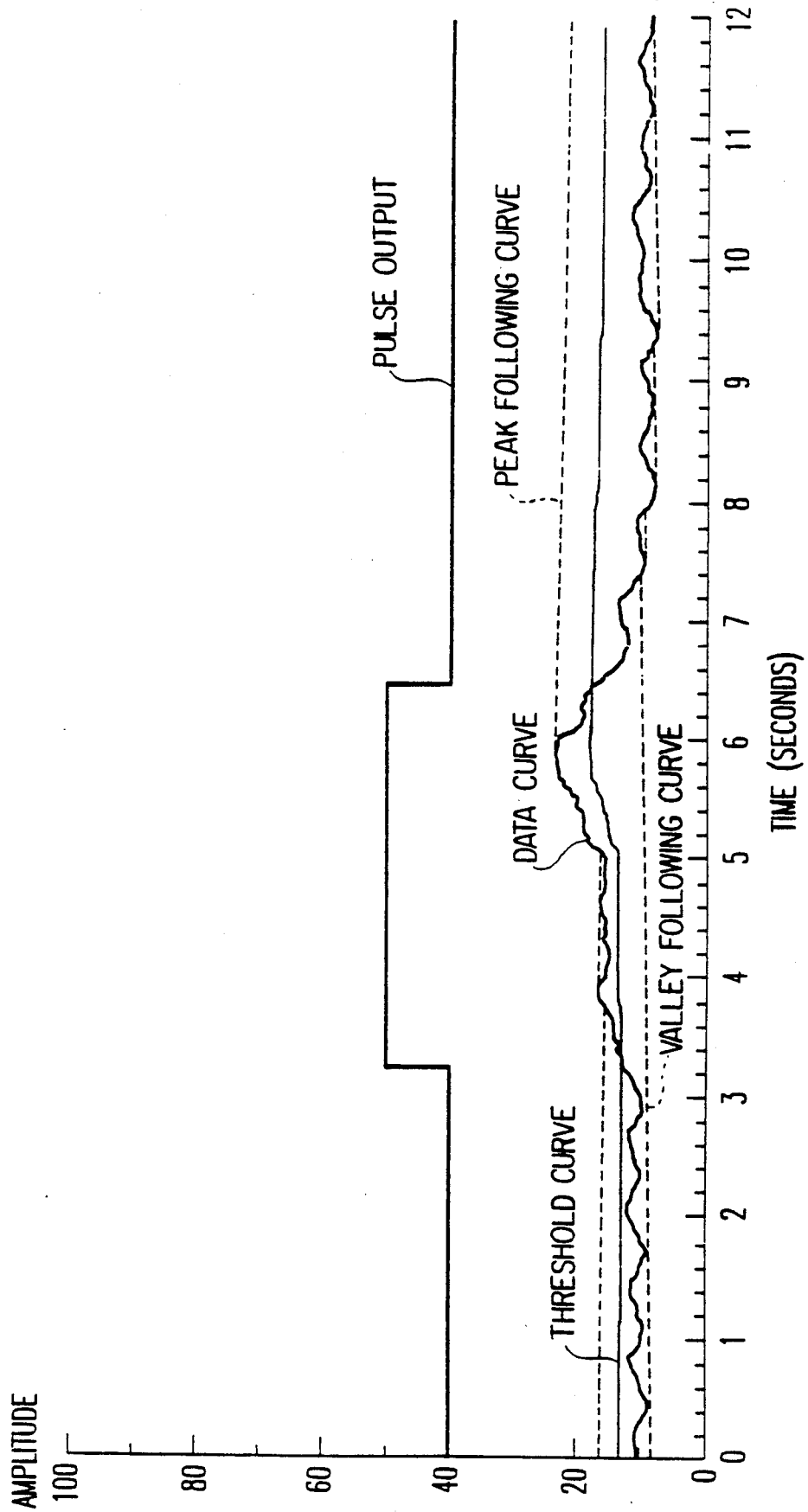
FIG. 7 is a graph illustrating adaptive thresholding performed by the breath event extraction circuit shown in FIG. 5.

The operation of the adaptive threshold circuit 120 is next explained with the aid of FIG. 7. Basically, the circuit 122 defines the threshold in terms of a predetermined percentage, e.g., 65%, between an upper peak-holding line representative of most recent peak signal at the output of filter 118 and a valley-holding line representative of most recent minimum signal at the output of filter 118. FIG. 7 shows data at the output of low-pass filter 118 having a ~0.2 Hz roll-off frequency.

Also shown as dotted lines are the peak-holding-line (above the data line), the valley-holding line (shown below the data line), and the threshold (about mid-way between the peak-holding-line and the valley-holdingline). The peak-holding-line is defined to never be below the data, and to slowly decay downwards whenever the data falls below that line. The decay rate is such as to bring the value to zero in about one minute, although values from ¼ min to 4 min may be used. Similarly, the valley-holding-line is defined to never be above the data, and to slowly rise whenever the data rises above that line. The rate of rise is sufficient to raise the line to the vicinity of the peak-holding line in about one minute although valves from ¼ min to 4 min may be used. Optionally, the initial rate of rise at initial turn-on may be faster (by about 10×), until the valley holding-line contacts the data line for the first time; this accelerates the start-up transient, establishing normal operation more quickly. Thus each of these lines is continually being reset, moving it away from the other, whenever the data touches that line, and at other times these lines slowly decay towards each other. The threshold is defined to lie at some predetermined fraction, such as 65%, of the way between the two lines. This fraction can range from ~35% to ~80%. Whenever the data line rises above the threshold line, the breath event is declared initiated. Whenever the data line returns back below the threshold line, the breath event is declared terminated.

In the above description various parameters have been described as being adjustable. It is to be understood that the present invention envisions that such parameters may also be "adaptive." An adaptive bandpass filter could be implemented in DSP, for example, by choosing the filter coefficients from a table representing a selection of filters. For example, for one of the sensor pad designs referred to above, the system would have stored in memory the coefficients for the following filters:

1) 25 Hz–50 Hz
2) 37 Hz–75 Hz
3) 50 Hz–100 Hz
4) 70 Hz–140 Hz
5) 100 Hz–200 Hz

A processor could periodically compare the "adjacent" filters (the next up and the next down) to the one in current use and check to see if the average amplitude of heart and breath signals is improved or deteriorated in those passbands; if one of the neighboring filters works better, it becomes the new "in use" filter. Sometime later, the same check will again be made of the signal strength when using the adjacent filter(s).

Alternatively, a switched capacitor filter could be used in an analog version of the signal processor for this invention. In such filters, the bandpass center frequency is shifted by changing the frequency of a control signal applied to a control port of the filter chip. One such chip is the MAX263 pin programmable bandpass filter manufactured by Maxim Integrated Products, 120 San Gabriel Drive, Sunnyvale, Calif. 94086.

Note that the above technique uses a fixed factor of 2× for the band limits. The DSP could instead, if desired, implement independent the band pass function with high-pass and low-pass filters in series, and independently adjust each roll-off frequency for best results, as described above, thereby adjusting the ratio of the roll-off frequencies as well as the center frequency. Similarly, the roll-off frequency of the filter 118 can be adaptively varied.

It will be understood by those versed in the art that there are many alternative ways in which the electronic subsystem of this invention can be implemented. In particular, we mention the following possibilities, which listing is not intended to be exhaustive:

1) The amplifier/limiter 61 may advantageously be implemented as an amplifier only, with the amplitude information in the noise current signal being preserved in addition to its frequency content.

2) Multiple optical detectors can be implemented, each with independent electronic sub-systems, each capable of triggering a shared or dedicated alarm based on different conditions, or each independently monitoring the same condition to provide more reliable detection of an abnormal state in the object being monitored.

3) Multiple frequency band sensing can be implemented electronically, by which means additional information about breathing dynamics can be derived.

4) The low-pass filter 118 of the breath extraction circuit could be implemented as a bandpass filter so that operation would be possible with positive and negative voltages instead of only positive voltages as above-described and as actually implemented in software.

5) Some or all of the functions shown in FIG. 5 as being performed with a Digital Signal Processor (DSP) can instead be implemented using analog electronic components in which case A/D 102 would not be needed.

6) As mentioned above, the adaptive adjustment of filter parameters can be automatically controlled by an AI (artificial intelligence) circuit, neural network, fuzzy logic, or other processor.

It will be further understood by one skilled in the art that a so-called single-mode fiber (or, more precisely, a double-mode fiber when both orthogonal polarizations are taken into account), while perhaps not the preferred embodiment because of its possibly greater cost and fragility, as well as the increased alignment accuracy that is required to couple light efficiently into it, is usable in this invention. Modal noise, while sometimes not as strong in single-mode fibers, does occur due to at least two causes. Firstly, bending of a single-mode fiber causes a change in the fraction of the guided light which is coupled to non-guided (lossy) higher-order modes, contributing to a change in guided optical power as the fiber moves. Secondly, in the case of a single mode fiber which guides both polarizations of light in a single transverse mode, part of the light guided in one polarization may be switched by fiber motion to the orthogonal polarization. Thus, in that case, a polarizer that is placed between the output end of the fiber and the optical detector, as discussed earlier as the "polarizing filter case," in position to intercept the full cone of light emerging from the fiber, will yield a strong modal noise current in the detector, since light in one polarization will not reach the detector and light in the other polarization will reach the detector nearly unattenuated. Indeed, it will be noted that the foregoing arrangement meets the criterion cited earlier for maximum noise current signal; namely, that the detector be coupled to half the guided modes. This single-mode fiber case is further advantaged in that, there being only one speckle cell, the fluctuations are of maximum possible amplitude, expressed as a percent of the total guided power, since the instantaneous power in the observed polarization mode ranges from 100% of the guided power to 0% of the guided power.

The smaller the number of modes guided by the optical fiber 2, the larger will be the RMS noise current when expressed as a fraction of the average photo current at detector 5. More particularly, the average photo current at detector 5 is essentially a constant proportional to the average total optical power guided by the fiber 2. Thus, in general, for a given laser input power, and assuming the photo detector intercepts half of the speckle cells, and neglecting input coupling losses and attenuation in the fiber 2 (both of which are typically small or negligible), the smaller the number of modes which the optical fiber 2 guides, the larger will be the RMS noise current expressed as a fraction of the total guided optical power. As is known, the number of modes which a fiber guides is proportional to the product of the fiber core diameter and the fiber numerical aperture, and is affected also by the radial distribution of the core's refractive index. It therefore follows that these fiber parameters should optimally be chosen to yield as few guided modes as possible, consistent with maintaining an appropriately broad tolerance on the precision with which the laser diode 1 and the input fiber end 21 need to be aligned for efficient and stable optical power input coupling, and with maintaining adequate mechanical ruggedness of the optical fiber. As noted above, these considerations may make the choice of a single-mode fiber less practical than a multimode fiber.

An improved plastic multimode optical fiber could be specially fabricated for this application to support significantly fewer guided modes than plastic step-index fibers currently available commercially. An example of such a specially prepared fiber would be one with a significantly smaller core diameter. Also, HCS (hard clad silica) glass fibers are appropriate for this invention. Plastic optical fibers which are readily available commercially typically have core diameters of 0.25 to 1.0 mm. A specially fabricated multimode plastic fiber with a core diameter of 50-100 μm, for example, would, as explained above, yield a significantly larger RMS noise current when expressed as a fraction of the average current. For example, a 50 μm core diameter fiber would yield a 100-fold increase in RMS modal noise current compared to an otherwise identical 0.5 mm core diameter fiber, since the number of modes supported is proportional to the cross-sectional area of the core, other factors being equal. Moreover, such a custom fiber would be significantly easier to align to a laser source than a single-mode fiber, for example. As will be appreciated, a larger RMS noise current will, in turn, result in simplified, lower-cost electronics with increased freedom from electronic amplifier noise effects, and/or increased sensitivity of the invention to mechanical motion of the optical fiber. Such an increase in sensitivity could, for example, be sufficient to enable the invention to more reliably monitor heartbeat, or to permit more reliable detection of breathing behaviors when the fiber is attached to a mattress cover and positioned under an infant. It should be also noted that 50 μm-250 μm core diameter fibers are readily available in glass or fused silica form. An example is the HCS fiber distributed by Ensign-Bickford Company. One such fiber has a step-index core diameter of 200 μm, a cladding diameter of 230 μm and a Tefzel TM plastic buffer of 500 μm diameter. While such fibers present an increased risk of breakage over plastic fibers in the current invention due to their greater brittleness, the use of glass or fused silica fibers may be practical in this invention provided the fibers are adequately protected by bend-resistant plastic buffer layers about the fiber. Thus, the invention is not restricted to the use of plastic fibers.

As noted above, the current invention can be used for monitoring a variety of bodily functions, as for example heartbeat and respiration during a medical treadmill test, or for monitoring irregularities in bodily function including, but not limited to, irregular, slow, fast, or interrupted breathing, and irregular, slow, fast, or interrupted heartbeat. This invention permits appropriate record-keeping mechanisms, notification mechanisms, or alarms to be triggered in response to abnormalities in the motion associated with these types of events.

Indeed, while the invention has been described in the context of its application to breathing monitoring and alarm and heartbeat monitoring and alarm, as well as the monitoring of motion producing bodily functions and for medical measurement applications such as treadmill testing and sleep monitoring, for example, it will be evident that the invention can also be used more generally to monitor and analyze the motions of any moving object to which an optical fiber can be compliantly coupled, or made to move with that object due to the motion of some intermediate agent such as a viscous fluid. Thus, all such applications are intended to be covered in the scope of this invention.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A fiber optic body motion monitor comprising:
   a light source;
   an optical fiber waveguide including an input end, an output end, and a sensing section intermediate said input and output ends, said optical fiber being positioned to receive light from said light source at said input end;
   movable means for transmitting motion of a body being monitored, said sensing section being coupled to said movable means so as to move therewith;
   photodetector means positioned proximate to said output end for receiving a speckle pattern of light therefrom, which pattern changes in response to movement of said sensing section, said photodetector means generating electrical signals representative of changes in said speckle pattern; and
   means for identifying electrical signals indicative of normal breathing and heartbeat motion and for differentiating them from electrical signals indicative of deviations from normal breathing and heartbeat motion, comprising,
   power determination means for producing a power signal indicative of an amount of power in a frequency band relevant to breathing and heartbeat in the signals generated by said photodetector means,
   breathing extraction means coupled to said power determination means for extracting from said power signal signals indicative of breathing of said body and outputting a signal indicative of the breathing of said body,
   heartbeat extraction means coupled to said power determination means for extracting from said power signal signals indicative of heartbeat of said body and outputting a signal indicative of the heartbeat of said body, and indicating means for producing at least one of a display indicative of at least one of the extracted breathing signals and the extracted heartbeat signals and an alarm when at least one of the extracted breathing signals and extracted heartbeat signals is indicative of a deviation from normal breathing and heartbeat motion, respectively.

2. The monitor according to claim 1, wherein said breathing extraction means comprises:
  low pass filter means for passing signals in a passband in which breathing signals have significant content;
  threshold means for detecting when signals passed by said bandpass filter means exceed a threshold; and
  processor means for generating said signal indicative of breathing based on signals detected by said threshold means.

3. The monitor according to claim 2, wherein said threshold means comprises an adaptable threshold detector which produces a varying threshold as a function of a difference between maximum and minimum levels of signals output by said low pass filter means.

4. The monitor according to claim 3, wherein said adaptable threshold detector resets said maximum and minimum levels to new levels at the level of the signal output by said low pass filter means whenever said signal output by said low pass filter means exceeds a present maximum level or falls below a present minimum level, respectively, and thereafter decreases said reset maximum level and increases said reset minimum level at predetermined rates.

5. The monitor according to claim 4, wherein said power determination means comprises a bandpass filter having a center frequency $f_{max}$ at which the breathing signals and heartbeat signals have greatest content and a passband of 0.33 to 3.0 $f_{max}$, and a rectifier, and the low pass filter of said breathing extraction means has a cutoff frequency of 0.5 Hz.

6. The monitor according to claim 5, wherein the bandpass filter of said power determination means has a passband of 0.50 to 2.0 $f_{max}$.

7. The monitor according to claim 1, wherein said heartbeat extraction means comprises:
  bandpass filter means for passing signals in a passband in which heartbeat signals have significant content;
  threshold means for detecting when signals passed by said bandpass filter means exceed a threshold; and
  processor means for generating said signal indicative of heartbeat based on signals detected by said threshold means.

8. The monitor according to claim 7, wherein said threshold means comprises:
  means for averaging the peak amplitudes of a predetermined number of peaks in the signals passed by said bandpass filter means; and
  means for setting a threshold equal to a predetermined percentage of the averaged peak amplitudes.

9. The monitor according to claim 7, wherein said power determination means comprises a bandpass filter having a center frequency $f_{max}$, at which the breathing signals and heartbeat signals have greatest content and a passband of 0.33 to 3.0 $f_{max}$, and a rectifier, and the bandpass filter means of said heartbeat extraction means has a 0.8–5.0 Hz passband.

10. The monitor according to claim 9, wherein the bandpass filter of said power determination means has a passband of 0.50 to 2.0 $f_{max}$.

11. The monitor according to claim 4, wherein said heartbeat extraction means comprises:
  bandpass filter means for passing integrated signals in a passband in which heartbeat signals have significant content;
  threshold means for detecting when signals passed by said bandpass filter means of said heartbeat extraction means exceed a threshold; and
  processor means for generating said signal indicative of heartbeats based on signals detected by said threshold means of said heartbeat extraction means.

12. The monitor according to claim 11, wherein said threshold means of said heartbeat extraction means comprises:
  means for averaging the peak amplitudes of a predetermined number of signals passed by said bandpass filter means of said heartbeat extraction means; and
  means for setting a threshold equal to a predetermined percentage of the averaged peak amplitudes.

13. The monitor according to claim 12, wherein said power determination means comprises a bandpass filter having a center frequency $f_{max}$, at which the breathing signals and heartbeat signals have greatest content and a passband of 0.33 to 3.0 $f_{max}$, and a rectifier, the low pass filter means of said heartbeat extraction means has a 0.8–5.0 Hz passband, and the low pass filter means of the breathing extraction means has a cutoff frequency of 0.5 Hz.

14. The monitor according to claims 1, 3, 8 or 13, wherein said photodetector means comprise a single photodetector positioned at a distance from said waveguide output end so as to intercept 24–74% of the speckles of light transmitted at said output end.

15. The monitor according to claims 1, 3, 8 or 13, wherein said photodetector means comprises a single photodetector, further comprising:
  filter means coupled to the output end of said optical fiber waveguide for reducing the number of speckles of light applied to said photodetector means to a range of 27–74% of the modes of light transmitted.

16. The monitor according to claims 1, 3, 8 or 13, wherein said photodetector means comprises:
  plural photoconductive elements disposed opposite to the end of said optical fiber waveguide so that said elements are illuminated by said speckle pattern of light, said elements producing a pair of outputs each representing approximately half of the speckle pattern of light incident on said elements; and
  differential amplifier means having a pair of inputs coupled to respective of the outputs produced by said plural photoconductive elements and an output which is a difference signal representing a difference between the *outputs produced by said plural photoconductive elements, said difference signal applied to said identifying means.

17. The monitor according to claim 16, wherein said plural photoconductive elements are positioned at a distance from the waveguide output end so as to intercept 33–100% of the speckles of light transmitted at said output end.

18. The monitor according to claim 16, wherein said plural photoconductive elements are positioned at a distance from the waveguide output end so as to intercept 45–83% of the speckles of light transmitted at said output end.

19. The monitor according to claim 18, wherein said plural photoconductive elements are positioned at a distance from the waveguide output end so as to intercept 60-70% of the speckles of light transmitted at said output end.

20. The monitor according to claim 16, comprising:
filter means coupled to the output end of said optical fiber waveguide for reducing the number of speckles of light applied to said photodetector means to a range of 33-100% of the speckles of light transmitted.

21. The monitor according to claim 20, wherein said filter means reduces the number of speckles of light applied to said photodetector means to 45-83%.

22. The monitor according to claim 21, wherein said filter means reduces the number of speckles of light applied to said photodetector means to 60-70%.

23. A fiber optic body motion monitor comprising:
a light source;
an optical fiber waveguide including an input end, an output end, and a sensing section intermediate said input and output ends, said optical fiber being positioned to receive light from said light source at said input end;
movable means for transmitting motion of a body being monitored, said sensing section being coupled to said movable means so as to move therewith;
photodetector means positioned proximate to said output end for receiving a speckle pattern of light therefrom, which pattern changes in response to movement of said sensing section, said photodetector means generating electrical signals representative of changes in said speckle pattern; and
means for identifying electrical signals indicative of normal breathing and heartbeat motion and for differentiating them from electrical signals indicative of deviations from normal breathing and heartbeat motion, comprising,
power determination means for producing a power signal indicative of an amount of power in a frequency band relevant to breathing in the signals generated by said photodetector means,
breathing extraction means coupled to said power determination means for extracting from said power signal signals indicative of breathing of said body and outputting a signal indicative of the breathing of said body, comprising,
low pass filter means for passing signals in a passband in which breathing signals have significant content,
threshold means for detecting when signals passed by said bandpass filter means exceed a threshold,
processor means for generating said signal indicative of breathing based on signals detected by said threshold means, and
indicating means for producing at least one of a display of said signal indicative of breathing and an alarm when said signal indicative of breathing is indicative of a deviation from normal breathing.

24. The monitor according to claim 23, wherein said threshold means comprises an adaptable threshold detector which produces a varying threshold as a function of a difference between maximum and minimum levels of signals output by said bandpass filter means.

25. The monitor according to claim 24, wherein said adaptable threshold detector resets said maximum and minimum levels to new levels at the level of the signal output by said low pass filter means whenever said signal output by said low pass filter means exceeds a present maximum level or falls below a present minimum level, respectively, and thereafter decreases said reset maximum level and increases said reset minimum level at predetermined rates.

26. The monitor according to claim 25, wherein said power determination means comprises a bandpass filter having a center frequency $f_{max}$ at which the breathing signals and heartbeat signals have greatest content and a passband of 0.33 to 3.0 $f_{max}$, and a rectifier, and the low pass filter means of said breathing extraction means has a cutoff frequency of 0.5 Hz.

27. The monitor according to claim 26, wherein said photodetector means comprises plural photoconductive elements positioned at a distance from the waveguide output end so as to intercept 33-100% of the speckles of light transmitted at said output end.

28. The monitor according to claims 23, 24, 25 or 26, wherein said photodetector means comprise a single photodetector positioned at a distance from said waveguide output end so as to intercept 24-74% of the speckles of light transmitted at said output end.

29. The monitor according to claims 23, 24, 25 or 26, comprising:
said photodetecting means comprising a single photodetector; and
filter means coupled to the output end of said optical fiber waveguide for reducing the number of speckles of light applied to said photodetector means to a range of 27-74% of the speckles of light transmitted.

30. The monitor according to claims 23, 24, 25 or 26, wherein said photodetector means comprises:
plural photoconductive elements disposed opposite to said optical fiber waveguide so that said elements are illuminated by said speckle pattern of light, said elements producing a pair of outputs each representing approximately half of the speckle pattern of light incident on said elements; and
differential amplifier means having a pair of inputs coupled to respective outputs produced by said plural photoconductive elements and an output which is a difference signal representing a difference between the outputs produced by said plural photoconductive elements, said difference signal applied to said identifying means.

31. The monitor according to claim 30, wherein said plural photoconductive elements are positioned at a distance from the waveguide output end so as to intercept 33-100% of the speckles of light transmitted at said output end.

32. The monitor according to claim 31, wherein said plural photoconductive elements are positioned at a distance from the waveguide output end so as to intercept 45-83% of the speckles of light transmitted at said output end.

33. The monitor according to claim 32, wherein said plural photoconductive elements are positioned at a distance from the waveguide output end so as to intercept 60-70% of the speckles of light transmitted at said output end.

34. The monitor according to claim 30, comprising:
filter means coupled to the output end of said optical fiber waveguide for reducing the number of speckles of light applied to said photodetector means to a range of 33-100% of the speckles of light transmitted.

35. The monitor according to claim 34, wherein said filter means reduces the number of speckles of light applied to said photodetector means to 45-83%.

36. The monitor according to claim 35, wherein said filter means reduces the number of speckles of light applied to said photodetector means to 60–70%.

37. A fiber optic body motion monitor comprising:
a light source;
an optical fiber waveguide including an input end, an output end, and a sensing section intermediate said input and out ends, said optical fiber being positioned to receive light from said light source at said input end;
movable means for transmitting motion of a body being monitored, said sensing section being coupled to said movable means so as to move therewith;
photodetector means positioned proximate to said output end for receiving a speckle pattern of light therefrom, which pattern changes in response to movement of said sensing section, said photodetector means generating electrical signals representative of changes in said speckle pattern; and
means for identifying electrical signals indicative of normal breathing and heartbeat motion and for differentiating them from electrical signals indicative of deviations from normal breathing and heartbeat motion, comprising,
power determination means for producing a power signal indicative of an amount of power in a frequency band relevant to heartbeat in the signals generated by said photodetector means,
heartbeat extraction means coupled to said power determination means for extracting from said power signal signals indicative of heartbeat of said body and outputting a signal indicative of the heartbeat of said body, comprising,
bandpass filter means for passing signals in a passband in which breathing signals have significant content,
threshold means for detecting when signals passed by said bandpass filter means exceed a threshold,
processor means for generating said signal indicative of heartbeats based on signals detected by said threshold means, and
indicating means for producing at least one of a display of said signal indicative of heartbeats and an alarm when said signal indicative of heartbeats is indicative of a deviation from normal heartbeats.

38. The monitor according to claim 37, wherein said threshold means comprises:
means for averaging the peak amplitudes of a predetermined number of signals previously passed by said bandpass filter means; and
means for setting a threshold equal to a predetermined percentage of the averaged peak amplitudes.

39. The monitor according to claim 37, wherein said power determination means comprises a bandpass filter having center frequency $f_{max}$ at which the breathing signals and heartbeat signals have greatest content and a passband of 0.33 to 3.0 $f_{max}$, and a rectifier, and the secondary bandpass filter means of said heartbeat extraction means has a 0.8–5.0 Hz passband.

40. The monitor according to claim 39, wherein the bandpass filter of said power determination means has a passband of 0.50 to 2.0 $f_{max}$.

41. The monitor according to claims 37, 38, or 40, wherein said photodetector means comprise a single photodetector positioned at a distance from said waveguide output end so as to intercept 24–74% of the speckles of light transmitted at said output end.

42. The monitor according to claims 37, 38, or 40, comprising:
said photodetector means comprising a single photodetector; and
filter means coupled to the output end of said optical fiber waveguide for reducing the number of speckles of light applied to said photodetector means to a range of 27–74% of the speckles of light transmitted.

43. The monitor according to claims 37, 38, or 40, wherein said photodetector means comprises:
plural photoconductive elements disposed opposite to said optical fiber waveguide so that said elements are illuminated by said speckle pattern of light, said elements producing a pair of outputs each representing approximately half of the speckle pattern of light incident on said elements; and
differential amplifier means having a pair of inputs coupled to respective outputs produced by said plural photoconductive elements and an output which is a difference signal representing a difference between the outputs produced by said plural photoconductive elements, said difference signal applied to said identifying means.

44. The monitor according to claim 43, wherein said plural photoconductive elements are positioned at a distance from the waveguide output end so as to intercept 33–100% of the speckles of light transmitted at said output end.

45. The monitor according to claim 44, wherein said plural photoconductive elements are positioned at a distance from the waveguide output end so as to intercept 45–83% of the speckles of light transmitted at said output end.

46. The monitor according to claim 45, wherein said plural photoconductive elements are positioned at a distance from the waveguide output end so as to intercept 60–70% of the speckles of light transmitted at said output end.

47. The monitor according to claim 43, comprising:
filter means coupled to the output end of said optical fiber waveguide for reducing the number of speckles of light applied to said photodetector means to a range of 33–100% of the speckles of light transmitted.

48. The monitor according to claim 47, wherein said filter means reduces the number of speckles of light applied to said photodetector means to 45–83%.

49. The monitor according to claim 48, wherein said filter means reduces the number of speckles of light applied to said photodetector means to 60–70%.

50. A fiber optic motion monitor comprising:
a light source;
an optical fiber waveguide including an input end, an output end, and a sensing section intermediate said input and output ends, said optical fiber being positioned to receive light from said light source at said input end;
movable means for transmitting motion of an object being monitored, said sensing section being coupled to said movable means so as to move therewith;
photodetector means positioned proximate to said output end for receiving a speckle pattern of light therefrom, which pattern changes in response to movement of said sensing section, said photodetector means generating electrical signals representative of changes in said speckle pattern; and means for processing said electrical signals to identify predetermined variations in said electrical signals, comprising, power determination means for producing a power signal indicative of an amount of power in a predetermined frequency band in the electrical signals generated by said photodetector means, extraction means coupled to said power determination means for extracting from said power signal signals indicative of said predetermined variations, a signal indicative of the predetermined variations comprising, filter means for passing signals in said predetermined frequency band in which predetermined variations have significant content, threshold means for detecting when signals passed by said filter means exceed a threshold, and processor means for generating said signal indicative of said predetermined variations based on signals detected by said threshold means, and indicating means for producing at least one of a display of said signal indicative of predetermined variations and an alarm when said signal indicative of predetermined variations is indicative of a deviation from a predetermined range.

51. The monitor according to claim 50, wherein said threshold means comprises an adaptable threshold detector which produces a varying threshold as a function of a difference between maximum and minimum levels of signals output by said filter means.

52. The monitor according to claim 51, wherein said adaptable threshold detector resets said maximum and minimum levels to new levels at the level of the signal output by said filter means whenever said signal output by said filter means exceeds a present maximum level or falls below a present minimum level, respectively, and thereafter decreases said reset maximum level and increases said reset minimum level at predetermined rates.

53. The monitor according to claim 52, wherein said photodetector means comprises a single photodetector positioned at a distance from said waveguide output end so as to intercept 24-74% of the speckles of light transmitted at said output end.

54. The monitor according to claim 52, comprising: said photodetecting means comprising a single photodetector; and filter means coupled to the output end of said optical fiber waveguide for reducing the number of speckles of light applied to said photodetector means to a range of 27-74% of the speckles of light transmitted.

55. The monitor according to claim 52, wherein said photodetector means comprises:

plural photoconductive elements disposed opposite to said optical fiber waveguide so that said elements are illuminated by said speckle pattern of light, said elements producing a pair of outputs each representing approximately half of the speckle pattern of light incident on said elements; and differential detector means having a pair of inputs coupled to respective outputs produced by said plural photoconductive elements and an output which is a difference signal representing a difference between the outputs produced by said plural photoconductive elements, said difference signal applied to said identifying means.

56. The monitor according to claim 55, wherein said plural photoconductive elements are positioned at a distance from the waveguide output end so as to intercept 33-100% of the speckles of light transmitted at said output end.

57. The monitor according to claim 56, wherein said plural photoconductive elements are positioned at a distance from the waveguide output end so as to intercept 45-83% of the speckles of light transmitted at said output end.

58. The monitor according to claim 57, wherein said plural photoconductive elements are positioned at a distance from the waveguide output end so as to intercept 60-70% of the speckles of light transmitted at said output end.

59. The monitor according to claim 55, comprising: filter means coupled to the output end of said optical fiber waveguide for reducing the number of speckles of light applied to said photodetector means to a range of 33-100% of the speckles of light transmitted.

60. The monitor according to claim 59, wherein said filter means reduces the number of speckles of light applied to said photodetector means to 45-83%.

61. The monitor according to claim 60, wherein said filter means reduces the number of speckles of light applied to said photodetector means to 60-70%.

* * * * *